US011332279B2

(12) United States Patent
Lowance et al.

(10) Patent No.: US 11,332,279 B2
(45) Date of Patent: May 17, 2022

(54) LIQUID DISPENSER APPARATUS

(71) Applicant: World Club Supply Corporation, Orange, CA (US)

(72) Inventors: Philip D. Lowance, Dana Point, CA (US); James Z. Monninger, Melbourne, FL (US)

(73) Assignee: WORLD CLUB SUPPLY CORPORATION, Orange, CA (US)

( * ) Notice: Subject to any disclaimer, the term of this patent is extended or adjusted under 35 U.S.C. 154(b) by 0 days.

(21) Appl. No.: 17/402,071

(22) Filed: Aug. 13, 2021

(65) Prior Publication Data

US 2022/0097911 A1 Mar. 31, 2022

Related U.S. Application Data

(60) Provisional application No. 63/083,593, filed on Sep. 25, 2020.

(51) Int. Cl.
*B65D 23/00* (2006.01)
*B65D 83/20* (2006.01)
*A47K 5/12* (2006.01)

(52) U.S. Cl.
CPC .......... *B65D 23/003* (2013.01); *A47K 5/1205* (2013.01); *B65D 83/20* (2013.01)

(58) Field of Classification Search
CPC ... B65D 23/003; B65D 83/20; B05B 11/0038; A47K 5/1205; A47K 2201/025
USPC ............................................... 222/180, 181.3
See application file for complete search history.

(56) References Cited

U.S. PATENT DOCUMENTS

| | | |
|---|---|---|
| 5,443,569 A | 8/1995 | Uehira et al. |
| 5,615,806 A | 4/1997 | Grothoff |
| D389,406 S | 1/1998 | Mascitelli |
| D434,984 S | 12/2000 | Wadsworth |
| D436,863 S | 1/2001 | Wadsworth et al. |
| D438,113 S | 2/2001 | Wsdsworth |
| D438,468 S | 3/2001 | Wadsworth |
| D438,798 S | 3/2001 | Wadsworth |
| 6,209,184 B1 | 4/2001 | Copeland et al. |
| 6,230,942 B1 | 5/2001 | Kuo |
| D471,105 S | 3/2003 | Fernandez |
| 6,536,630 B1 | 3/2003 | Chan et al. |
| 6,604,656 B1 | 8/2003 | Tseng |

(Continued)

FOREIGN PATENT DOCUMENTS

| | | | |
|---|---|---|---|
| DE | 202015103187 U1 | * | 6/2016 |
| WO | WO 2009/138434 A1 | * | 11/2009 |
| WO | 2020059945 A1 | | 3/2020 |

OTHER PUBLICATIONS

International Search Report, PCT/US2021/050990 and Written Opinion of the International Searching Authority, dated Feb. 17, 2022, 18 pages.

*Primary Examiner* — Lien M Ngo
(74) *Attorney, Agent, or Firm* — Lapple Ubell IP Law, LLP; Franklin D. Ubell

(57) ABSTRACT

A liquid dispenser apparatus having a back plate, a housing, and a liquid dispenser unit, the housing and backplate being constructed to attach to one another, the housing and liquid dispenser unit being constructed such that the liquid dispenser unit is removably installable into the housing and pivotally mounted with respect thereto such that the dispenser unit can be pivoted to a selected acute filling angle with respect to the housing.

28 Claims, 31 Drawing Sheets

(56) References Cited

U.S. PATENT DOCUMENTS

| | | |
|---|---|---|
| D479,985 S | 9/2003 | Lowance |
| 6,695,176 B1 | 2/2004 | Nazari |
| D489,614 S | 5/2004 | Pinnavaia |
| 6,820,770 B2 * | 11/2004 | Makino .................... A47K 5/12 |
| | | 222/180 |
| 6,966,459 B1 | 11/2005 | Tseng |
| 7,025,924 B2 | 4/2006 | Lowance |
| D527,258 S | 8/2006 | Crawford |
| 7,168,594 B2 | 1/2007 | Law et al. |
| D536,973 S | 2/2007 | van der Heijden et al. |
| D588,006 S | 3/2009 | Boes et al. |
| D598,750 S | 8/2009 | Boes et al. |
| D600,553 S | 9/2009 | Dubitsky et al. |
| D600,554 S | 9/2009 | Toh et al. |
| D604,610 S | 11/2009 | Ames et al. |
| D636,262 S | 4/2011 | Michitsuji et al. |
| 8,034,281 B2 | 10/2011 | Lowance |
| D666,911 S | 9/2012 | Modha et al. |
| D678,064 S | 3/2013 | Arminak |
| 9,655,478 B2 | 5/2017 | Muderlak et al. |
| 9,687,866 B1 | 6/2017 | Chan |
| D792,218 S | 7/2017 | Chan |
| D794,452 S | 8/2017 | Chan |
| 10,182,685 B2 * | 1/2019 | Ophardt ............... A47K 5/1205 |
| 10,750,911 B2 * | 8/2020 | McDonagh .............. A47K 5/12 |
| 10,959,503 B2 | 3/2021 | Bilton et al. |
| 2005/0284888 A1 * | 12/2005 | Rhodenbaugh .......... A47K 5/12 |
| | | 222/181.3 |
| 2007/0210110 A1 * | 9/2007 | Anhuf ...................... A47K 5/12 |
| | | 222/180 |
| 2008/0006656 A1 | 1/2008 | Tseng |
| 2008/0290119 A1 | 11/2008 | Tseng |
| 2010/0135834 A1 | 6/2010 | Tseng |
| 2011/0259920 A1 | 10/2011 | Rennie et al. |
| 2012/0181405 A1 | 7/2012 | Zlatic et al. |
| 2015/0041560 A1 | 2/2015 | Cheng et al. |
| 2016/0040455 A1 * | 2/2016 | Limbert ............... A47K 5/1211 |
| | | 222/153.09 |
| 2016/0167073 A1 * | 6/2016 | Notarianni .......... B05B 11/3014 |
| | | 222/153.09 |
| 2017/0105584 A1 * | 4/2017 | Ophardt ............. B05B 11/3014 |
| 2017/0144176 A1 | 5/2017 | Toh et al. |
| 2018/0306180 A1 | 10/2018 | Chan et al. |
| 2019/0210050 A1 | 7/2019 | Fields et al. |
| 2019/0329275 A1 | 10/2019 | Toh et al. |
| 2019/0366378 A1 * | 12/2019 | Langlotz ................. B05B 15/62 |
| 2019/0374071 A1 | 12/2019 | Bai |
| 2020/0029748 A1 * | 1/2020 | Bradley .................. A47K 5/12 |
| 2020/0197966 A1 | 6/2020 | Marshall et al. |
| 2021/0187530 A1 | 6/2021 | Lee et al. |

\* cited by examiner

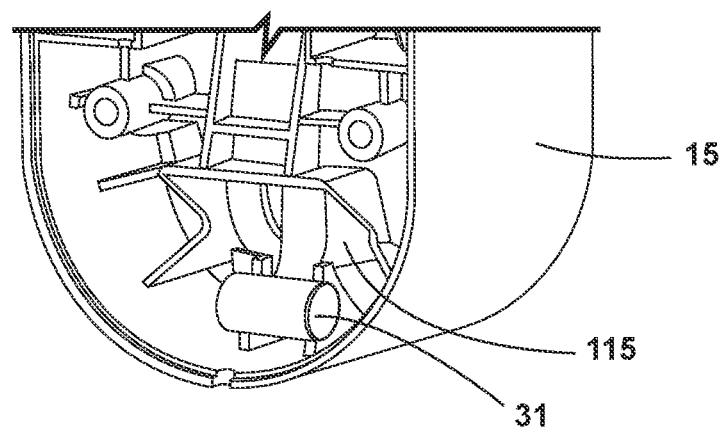
FIG. 19
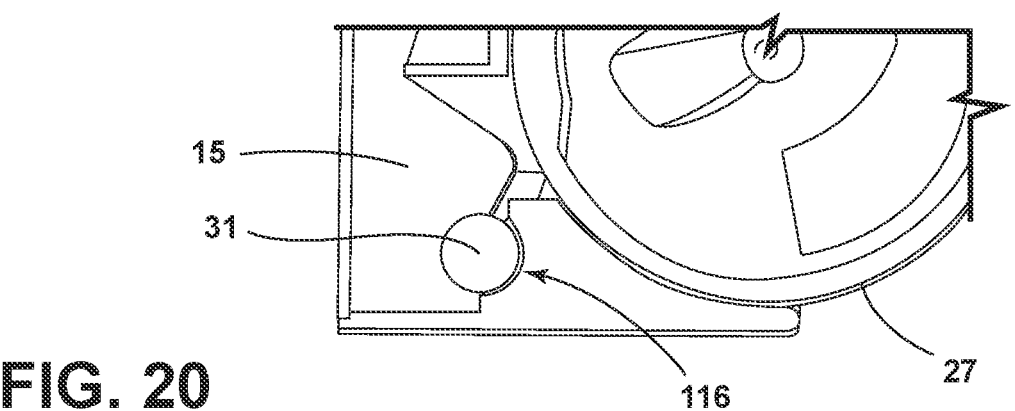
FIG. 20
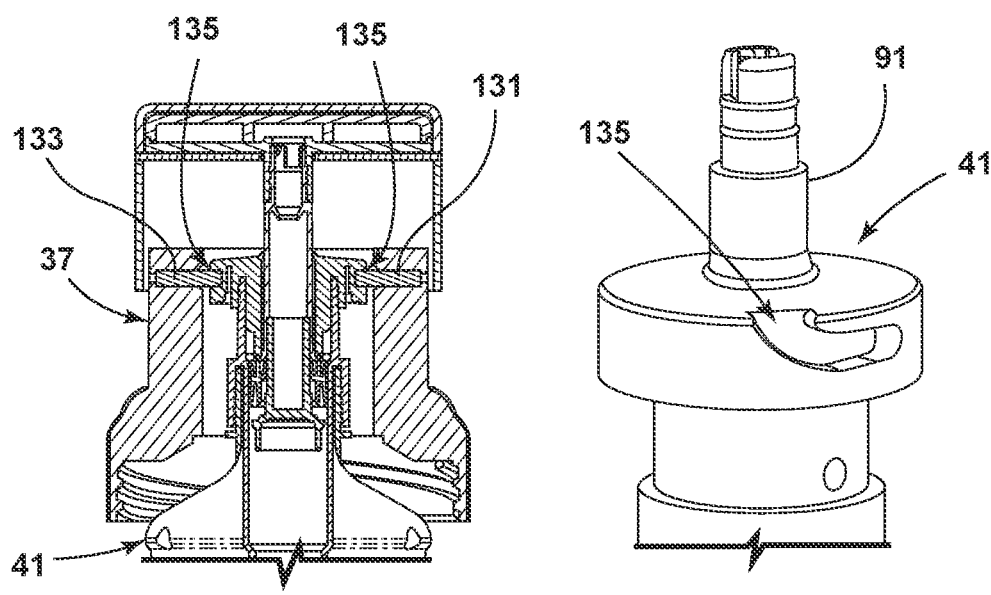
FIG. 21
FIG. 22

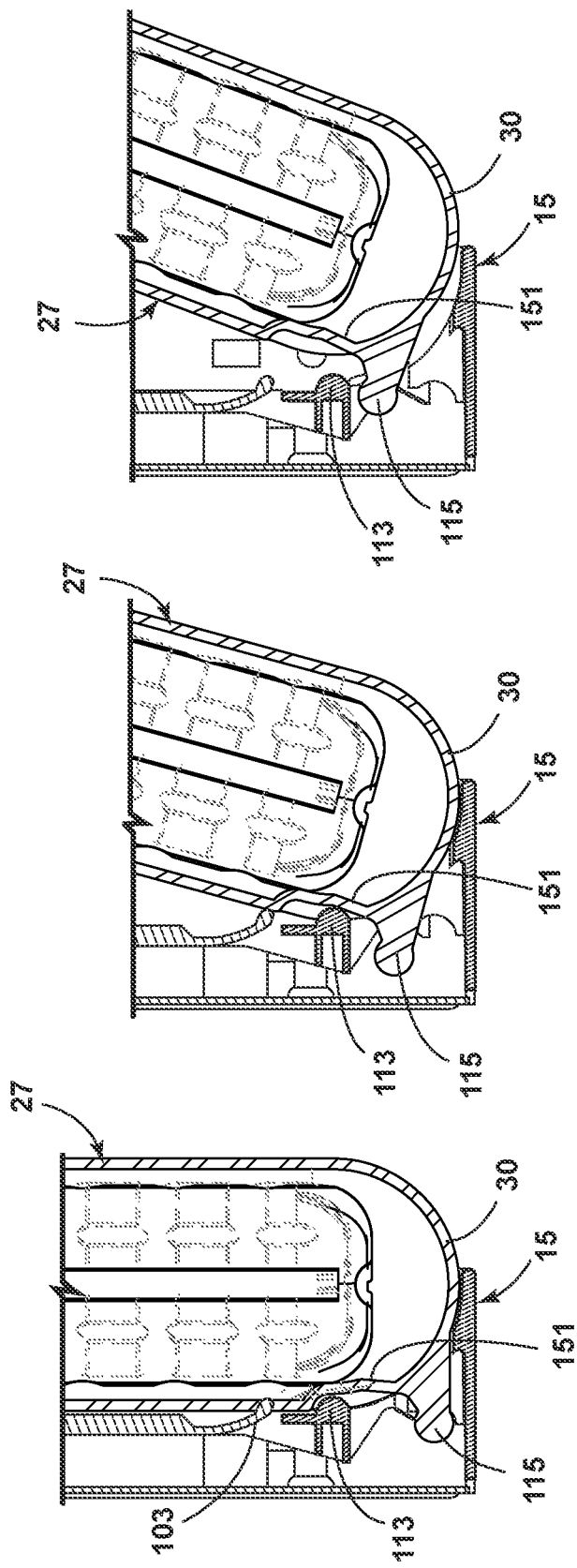

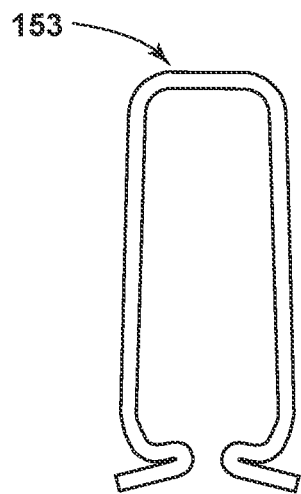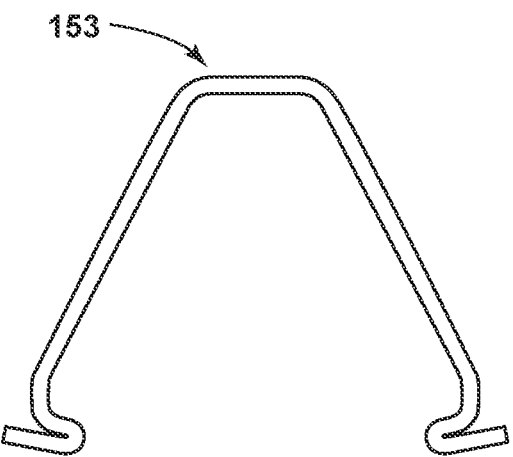
FIG. 32     FIG. 33
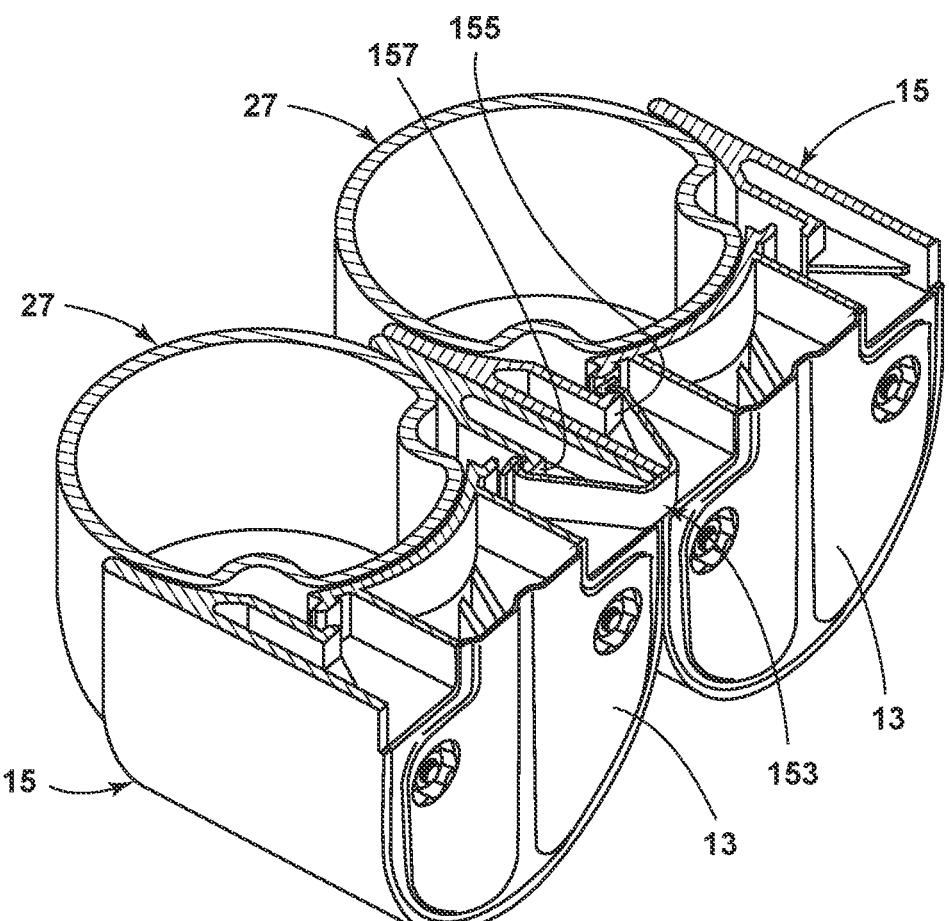
FIG. 34

LIQUID DISPENSER APPARATUS

CROSS REFERENCE TO RELATED APPLICATIONS

This application claims the benefit of and priority to U.S. Provisional Patent Application Ser. No. 63/083,593, filed Sep. 25, 2020, and entitled, "Liquid Dispenser Apparatus," the contents of which is hereby incorporated by reference herein in its entirety.

FIELD OF THE INVENTION

The subject disclosure relates to apparatus for dispensing liquids, such as, for example and without limitation, lotions, hair products, skin products, massage products, hygienic products, dental products, sun care products, inhalant, food products, and more specifically and without limitation: hair shampoo, hair conditioner, hair gel, skin moisturizer, body fragrance, body wash, hand soap, shave crème, massage lotion, massage crème, massage oil, hand sanitizer gel, antibacterial skin soap, tooth paste, mouthwash, sun block, tanning oil, after sun crème, eucalyptus oil, coffee creams, coffee flavors, coffee sweeteners, mustard, ketchup, and mayonnaise.

DESCRIPTION OF RELATED ART

Various devices for dispensing various liquids have been developed in the past.

SUMMARY OF ILLUSTRATIVE EMBODIMENTS

According to one illustrative embodiment, a liquid dispenser apparatus may comprise a back plate, a housing, and a liquid dispenser unit, the housing and backplate being constructed to attach to one another, the housing and liquid dispenser unit being constructed such that the liquid dispenser unit is removably installable into the housing and pivotally mounted with respect thereto such that the dispenser unit is pivotable to a selected acute angle with respect to the housing. In other illustrative embodiments, a liquid dispenser apparatus may comprise any one or any combination of the following features:

(a) a pump, a pump top, a closure having a lower skirt portion, a cartridge for storing liquid to be dispensed, and a canister, the canister being shaped to receive and house the cartridge;

(b) a reservoir for storing liquid to be dispensed and comprising a plastic material, the reservoir being attached by a leak-proof seal to the pump wherein the reservoir may be, for example, a cylindrical cartridge or a plastic bag;

(c) a lower skirt portion including a hook on a side surface thereof which may be u-shaped or of other shape, the lower skirt portion and canister being configured to removably attach together;

(d) a pump top comprising four mating components including a top cap component, a bottom cap component, and upper and lower intermediate components, the top cap component including two threaded bosses on an underside thereof, the upper and lower mating intermediate components having mating openings and mating notches formed therein, the lower intermediate component further having a liquid dispensing opening, a liquid receiving boss, and first and second vertically depending tangs formed on either side of the liquid dispensing opening, the tangs being configured to snap-fittingly engage a liquid dispensing opening of the bottom cap component;

(e) an interior rear housing surface including first and second back surface positioning arms, first and second resilient side retaining arms, and first and second side pivot bumps;

(f) side pivot bumps on a housing positioned to fit into respective pivot notches formed on opposite lower sides of a canister to enable pivotal movement of the canister with respect to the housing about a horizontal axis defined by the first and second side bumps;

(g) resilient side arms having ends configured to snap into respective indentations in an outer surface of a canister in order to position and retain a liquid dispenser unit in an installed position in a housing;

(h) resilient positioning arms positioned to support a back surface of a canister;

(i) a locking mechanism comprising a ferromagnetic locking pin insertable into an aperture in a rear of a housing and through an opening in a hook located on the apparatus;

(j) a pump top wherein upper and lower intermediate components of the pump top are fused together to create a hollow, sealed assembly which provides a path through which a stored liquid travels to a dispensing opening in the lower intermediate component and then to a dispensing opening in a bottom component; wherein a stem of a pump passes through a hole in a bottom cap component and fits into a boss of the lower intermediate component to enable supply of stored liquid to the fused together intermediate components; wherein top and bottom cap components sandwich the fused-together intermediate components; and wherein, in assembly, first and second guide pins pass through holes in the bottom cap component, through holes and notches in each of the intermediate components, and thread into the threaded bosses on the underside of the top cap component;

(k) a lower skirt portion and canister which threadably engage with one another;

(l) a pump having a track formed on a side surface thereof shaped to engage a pin on a closure and configured to enable the pump to removably attach to the closure;

(m) a pump which fits into and is sealingly attached to a liquid-containing cartridge;

(n) an attachment member positioned on a back surface of a canister and configured to engage first and second latches formed on a housing in order to enable removable attachment of the canister to the housing. In one embodiment, the attachment member may be hook-shaped;

(o) a bottom tang positioned on a back surface of a canister in order to facilitate removable attachment of the canister to a housing;

(p) a drip tray positioned beneath a housing and removably attachable thereto;

(q) a drip tray comprising first and second horizontally projecting tongues which comprise part of a snap-fit attachment mechanism for attaching the drip tray to a housing;

(r) a liquid dispenser apparatus so configured that, to remove a canister thereof, the canister is rotated forward to an acute angle wherein it rests under its own weight and wherein physically pulling the canister further downward causes a shoulder surface of an attachment member to react with a surface of the housing so as to disengage the canister from side pivot bumps;

(s) a snap-fit engagement mechanism comprising a ramp having a vertical retaining ridge and wherein an upper tongue of a drip tray flexes up and a lower cross bar of the upper tongue snaps over a retaining ridge thereby preventing removal of the drip tray by simply pulling it out;

(t) a drip tray snap engagement mechanism so configured that a tool may be inserted through an opening in a housing so as to engage an upper cross bar of a flexible tongue and then flex the tongue upwards to allow removal of the drip tray;

(u) a flexure in a housing which preloads a lower tongue of a drip tray into a channel of the housing;

(v) a drip tray including a spherical area which matches a bottom spherical shape of a canister and further includes one or more raised bumps which protrude and create a physical interference between the drip tray and canister such that the act of installing the canister into a housing applies force to the drip tray, preloading it into place; and/or (w) a shroud shaped to encase the exterior of a closure and which provides a bearing surface on which a pump top rides.

(x) a housing which includes an upper portion having parallel outer side surfaces and a circularly contoured inner surface which is shaped and dimensioned to partially surround, protect and shield a pump top.

Illustrative embodiments further comprise first and second tracks located on opposite sides of a pump and shaped to engage respective pins located on a cooperating member of a liquid dispensing apparatus so as to enable attachment of the pump to the cooperating member by engaging the tracks with the pins and turning the pump. In one embodiment, the tracks can each be ¼ style tracks but may be of other style or other selected angle in other embodiments. Thus, an illustrative embodiment may comprise a pump attached to a liquid containing cartridge or bag so as to create a leak proof seal and wherein the pump comprises tracks located on opposite sides thereof and shaped to engage respective pins located on a cooperating member of a liquid dispensing apparatus so as to enable attachment of the pump to the cooperating member by engaging the tracks with pins and turning the pump. In various embodiments, the cooperating member may be a closure component of a liquid dispensing apparatus.

Illustrative embodiments further include a pump attached to an open end of a liquid containing cartridge so as to create a leak proof seal between the pump and cartridge. In one embodiment, the cartridge comprises or may be formed of recyclable plastic but may be formed of other materials in other embodiments. In one embodiment, the cartridge may be cylindrically shaped or of circular cross-section but may be of other shapes in other embodiments. Thus, an illustrative embodiment may comprise a pump attached to an open end of a liquid containing cartridge having a cylindrical liquid-containing portion so as to create a leak-proof seal between the pump and cartridge and wherein the cartridge is formed of a recyclable plastic.

DESCRIPTION OF THE DRAWINGS

FIG. 19 is a partial perspective sectional view of the housing component illustrating a canister attachment mechanism according to an illustrative embodiment;

FIG. 20 is a partial side sectional view further illustrating the canister attachment mechanism;

FIG. 21 is a partial side sectional view illustrating a pump attachment mechanism according to an illustrative embodiment;

FIG. 22 is a partial perspective view further illustrating the pump attachment mechanism;

FIGS. 29-31 are partial side sectional views illustrating a sequence of canister positions during a leveraged removal of the canister of the illustrative embodiment from the housing;

FIG. 32 is a front view of a clip for joining adjacent housings according to an illustrative embodiment;

FIG. 33 is a front view illustrating the clip of FIG. 25 in a spread apart state;

FIG. 34 is a partial perspective sectional view illustrating a clip according to FIG. 26 joining two adjacent housings in an illustrative embodiment;

DETAILED DESCRIPTION OF ILLUSTRATIVE EMBODIMENTS

Figure 5:
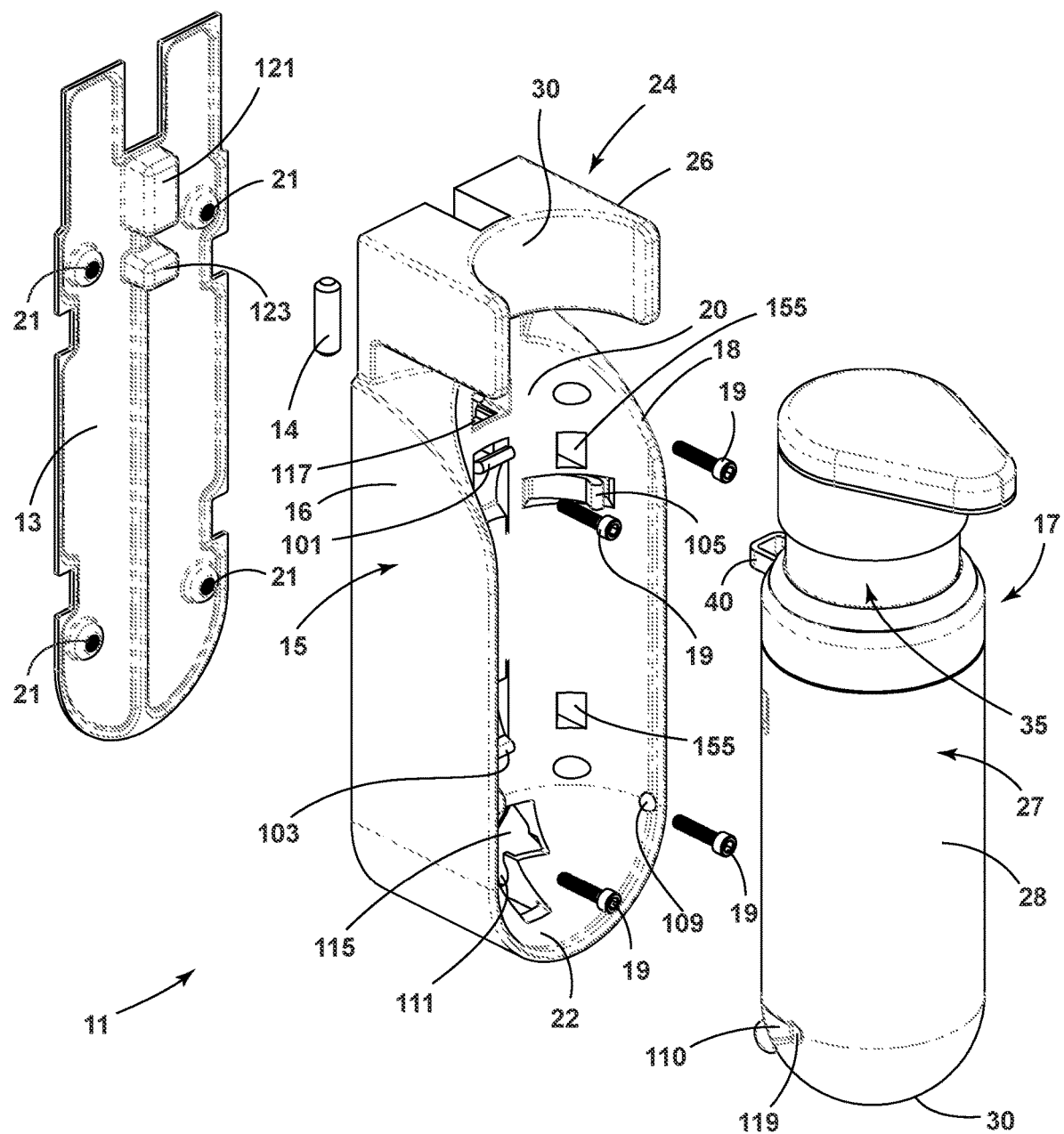
FIG. 5 is an exploded side perspective view of the apparatus of FIG. 1.

FIGS. 1-5 depict an illustrative embodiment of a liquid dispenser apparatus 11. The dispenser apparatus 11 includes a back plate 13, a housing 15, and a liquid dispenser unit 17. FIG. 5 also illustrates a ferromagnetic locking pin 14, which forms part of a locking mechanism described in more detail below.

In one embodiment, the housing 15 is attached to the back plate 13 by suitable fastening devices, for example, such as mechanical fastening devices such as screws 19, which may thread into suitable bosses 21 in the back plate 13. In one embodiment, the back plate 13 is fabricated of a suitable metal, such as, for example, stainless steel, and the housing 15 may be formed of ABS, polycarbonate or other suitable plastic in various embodiments. The back plate 13 and housing 15 may be fabricated of other materials in other embodiments. In the illustrative embodiment, the back plate 13 includes a centrally positioned vertical groove or depression 141, which provides rigidity and a drainage path down the back wall 16 of the back plate 13.

In one embodiment, the back plate 13 may be attached to a surface such as a wall by double sided adhesive tape. In other embodiments, the housing 15 may be attached to a suitable surface by other fastening mechanisms, for example, such as mechanical fasteners.

Figure 1:
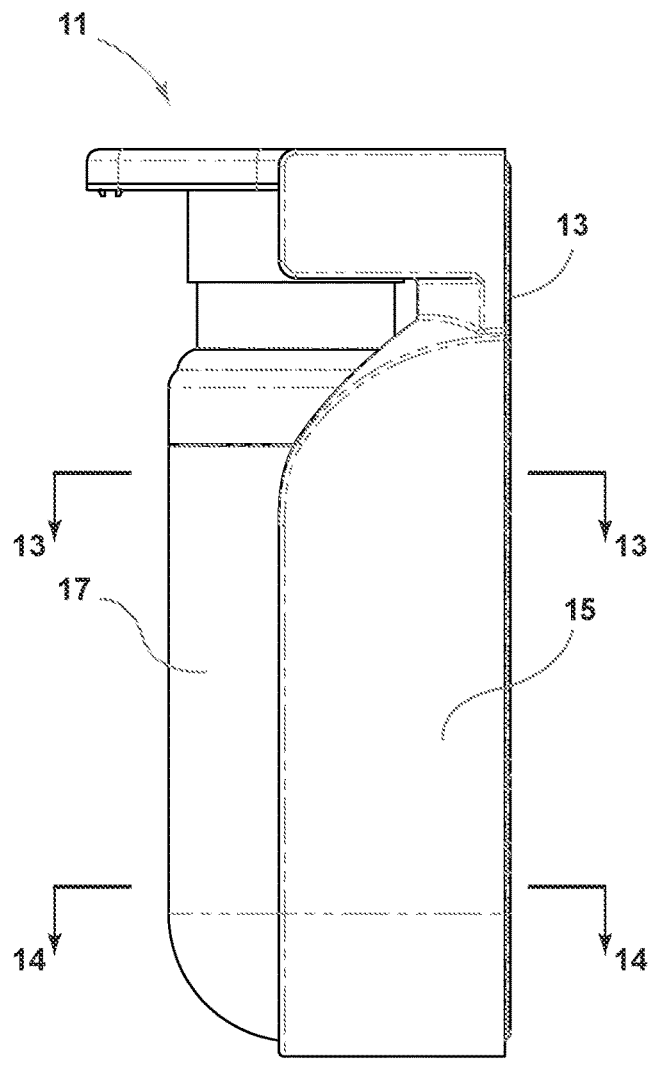
FIG. 1 is a side view of a liquid dispenser apparatus according to an illustrative embodiment.
Figure 2:
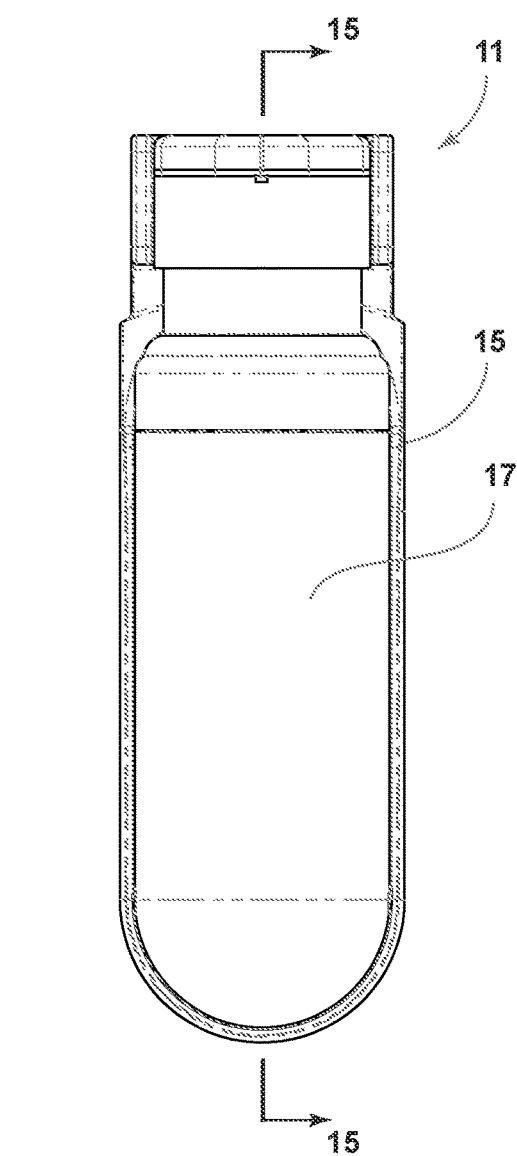
FIG. 2 is a front view of the dispenser apparatus of FIG. 1.
Figure 3:
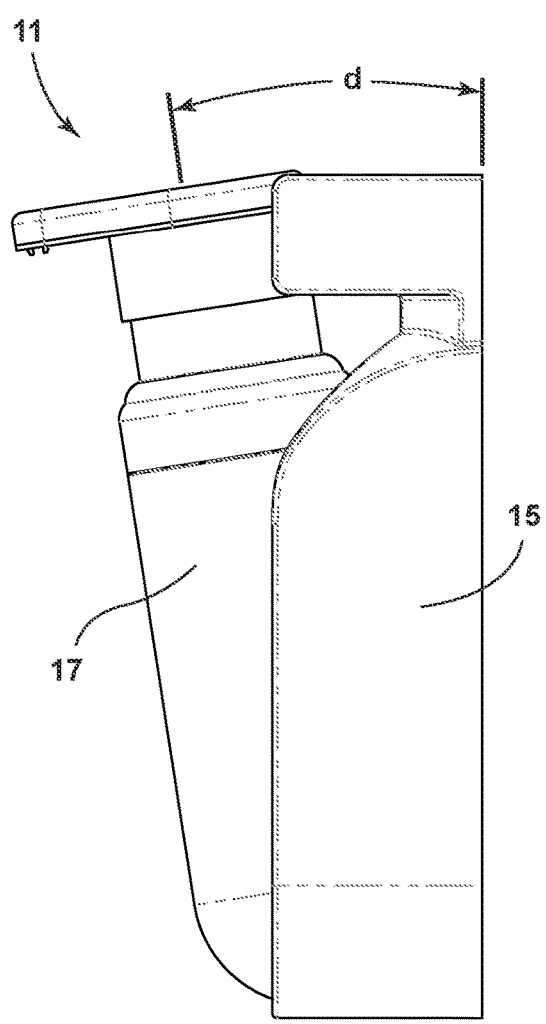
FIG. 3 is a side view of the dispenser apparatus of FIG. 1 in a service position.
Figure 4:
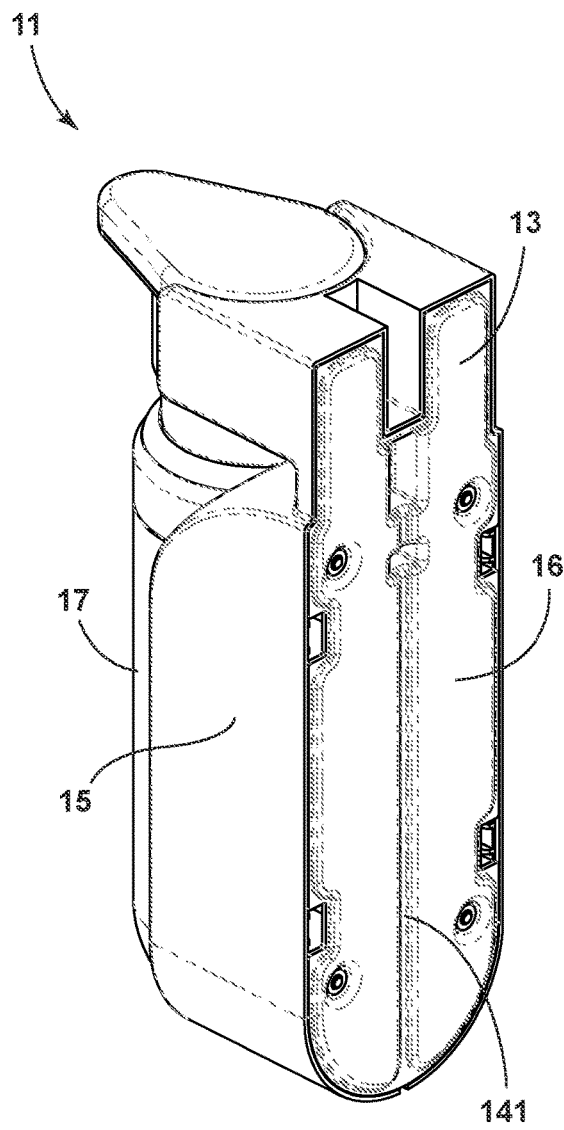
FIG. 4 is a rear perspective view of the dispenser apparatus of FIG. 1.

In one embodiment, the liquid dispenser unit 17 snap-fits into the housing 15 and may be pivotally mounted thereto so that it may be pivoted to a filling (servicing) position, such as shown in FIG. 3. In illustrative embodiment of FIG. 3, the pivot angle "alpha" between the housing 15 and the liquid dispenser unit 17 is twenty (20) degrees but could be other acute angles in various other embodiments. The "service" position is used to change cartridges 25 (FIG. 6) and is fully extended at the 20-degree position, where a physical stop supports the canted weight of the dispenser unit 17.

Figures 6, 7:
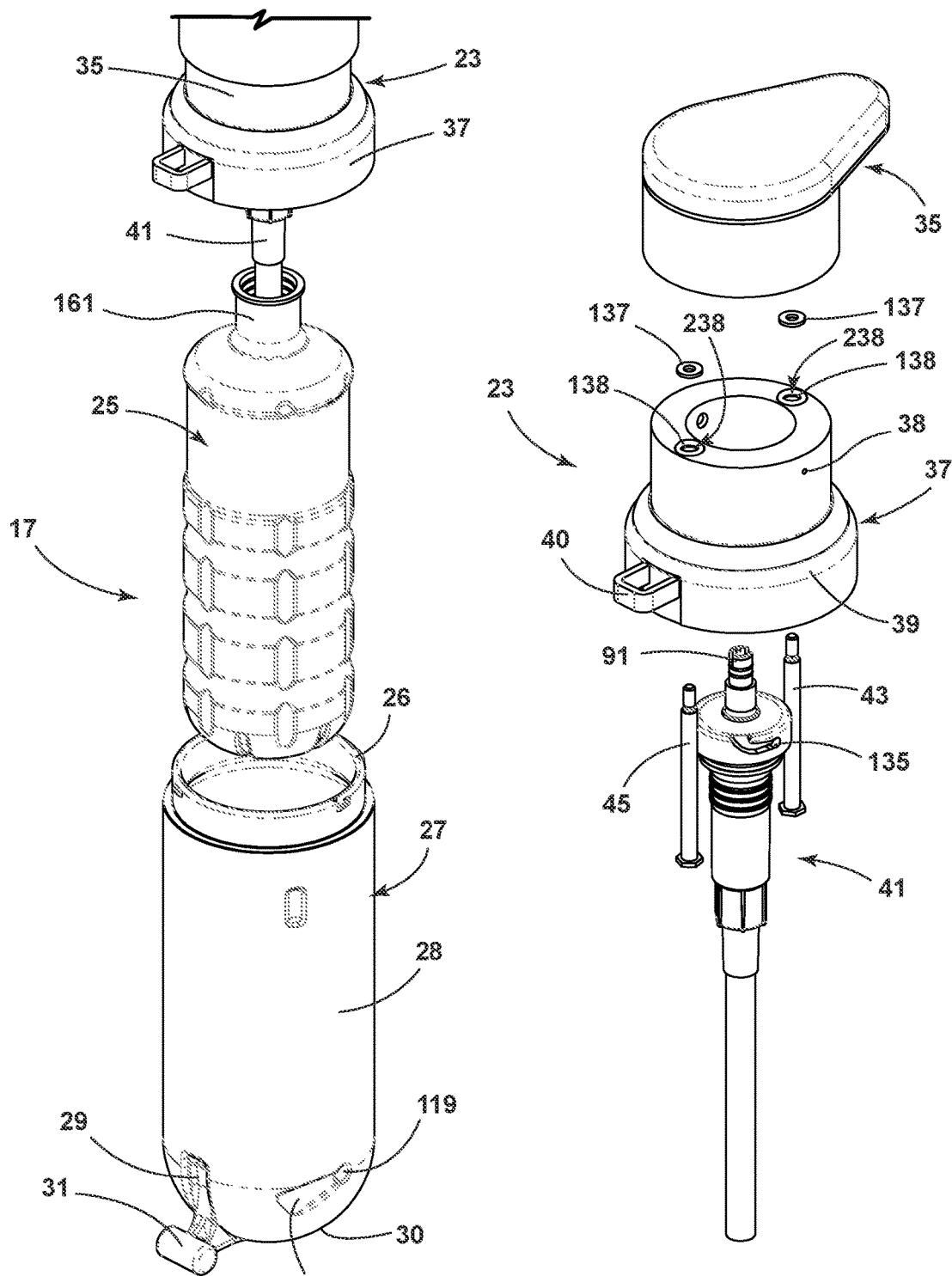
FIG. 6 is an exploded perspective of the liquid dispensing unit of the apparatus of FIG. 1.
FIG. 7 is an exploded perspective view of componentry of the apparatus of FIG. 6.

As shown in FIG. 6, in the illustrative embodiment, the liquid dispenser unit 17 may comprise a closure 37 with pump top 35, a pump 41, a replaceable cartridge 25, and a canister 27. The canister 27 includes a bottom tang 31 mounted in a tang groove 29 to facilitate pivotal attachment to the housing 15. In the illustrative embodiment, the cartridge 25 contains liquid to be dispensed and snugly fits into the canister 27.

In assembly in one illustrative embodiment, the pump top 35 and closure 37 are attached together. The pump 41 is attached to the cartridge 25 and the pump 41 is then connected to the closure 37. Finally, the closure 37 with pump 41 and cartridge 25 attached is attached to the canister 27, for example by a threaded engagement between the closure 37 and the canister 27. In one embodiment, the engagement may be "keyed" so that the closure 37 and pump top 35 can only assume one position with respect to the canister 27. Illustrative structure for interconnecting the various components as just described is discussed in more detail below.

In an illustrative embodiment, the replaceable cartridge 25 comprises a reservoir for liquid to be dispensed and is formed of thin walled plastic which can be crushed in the hand, similar to that used in some purified water bottles. In one embodiment, texture is added to the plastic wall via forming a matrix of squares or rectangles or other shapes to provide rigidity. Such cartridges 25 may be filled by high speed rotary filling machines like those used to bottle bottled water and which may fill, for example, 1,000 units per minute. After filling, a pump 41 is attached to the cartridge via a leak-proof seal. Cartridges 25 may be formed of other materials and made by other processes in other embodiments. The cartridges 25 are thus formed of readily recyclable material and hence are environmentally friendly.

In another illustrative embodiment, the cartridge 25 is stretch-blow molded from a thermoplastic material in a fashion similar to the blow molding processes for plastic bottles. After the cartridge is filled with liquid to be dispensed, a pump 41 is permanently press-fit into the cartridge neck 161 (FIG. 6), producing a leak proof seal with the pump 41 to draw and dispense the liquid contents from the cartridge 25.

In another illustrative embodiment, a reservoir for the liquid to be dispensed is formed using a Form/Fill/Seal ("FFS") process using flexible plastic film such as HDPE or LLDPE to form a plastic bag containing the desired liquid to be dispensed. In an illustrative embodiment, after the bag is filled with liquid to be dispensed, a pump 41 is heat sealed into a seam of the bag to produce a leak-proof seal. In one illustrative embodiment, a conventional pump 41 has a fitment integrated into the injection molded barrel of the pump called a "Boat" due to its shape. The Boat shape is most easily and leak resistantly sealed into a seam on the FFS container. In another illustrative embodiment, the fitment is a grommet that is thermo welded to the sheet stock that then forms the bag. After filling, a pump is then pressed into the grommet fitment to establish a leak-proof seal. In illustrative embodiments, the pouch/bag material is fully recyclable as is the pump.

In another embodiment, a cartridge 25 is produced as a thermoformed cup with an open top and flat rim. Additionally, a lid is created for the cup from an injection molded and integrated part of the pump. Therefore, in such an embodiment, every pump 41 has an integrated concentric lid that the pump stem passes through. After filling the cup with liquid, the lid and integrated pump are induction sealed to the flattened rim of the plastic cup, forming a leak proof seal with the filled cup from which the liquid contents can be dispensed. As noted above, in other embodiments, the canister 27 could be filled directly with liquid rather than employing cartridges 25.

As seen in FIG. 6, in the illustrative embodiment, the canister 27 has a circular open top end 26, a cylindrical central section 28, and a spherically contoured bottom surface 30. The housing 15 has flat side surfaces 16, 18 (FIG. 5) spaced apart and shaped to receive the canister 27. In the illustrative embodiment, the interior back surface 20 of the canister receiving portion of the housing 15 may be circularly contoured and the bottom interior surface 22 spherically contoured to mate with the corresponding surfaces 28, 30 of the canister 27 and to provide a "ball and socket" tilting action. In the illustrative embodiment, the housing 15 further includes an upper portion 24, which has parallel outer side surfaces 26, 28 and a circularly contoured inner surface 30, which is shaped and dimensioned to partially surround and shield the pump top 35.

As illustrated in FIG. 7, the pump unit 23 of the illustrative embodiment includes a pump head 35, a closure 37 having a cylindrical upper portion 38 a lower skirt 39, and a pump 41. The pump 41 includes a pump stem 91 and a groove or track 135, which forms part of a mechanism for attaching the pump 41 to the closure 37, as described in more detail below. The lower skirt 39 includes a u-shaped hook 40 on a side surface thereof, which forms part of a locking mechanism described in further detail below. The closure 37 includes bores 238 surrounded by O-rings 138 through which the guide pins 43, 45 pass. In one embodiment, the pump 41 may employ a conventional spring-loaded internal pumping mechanism.

Figure 9:
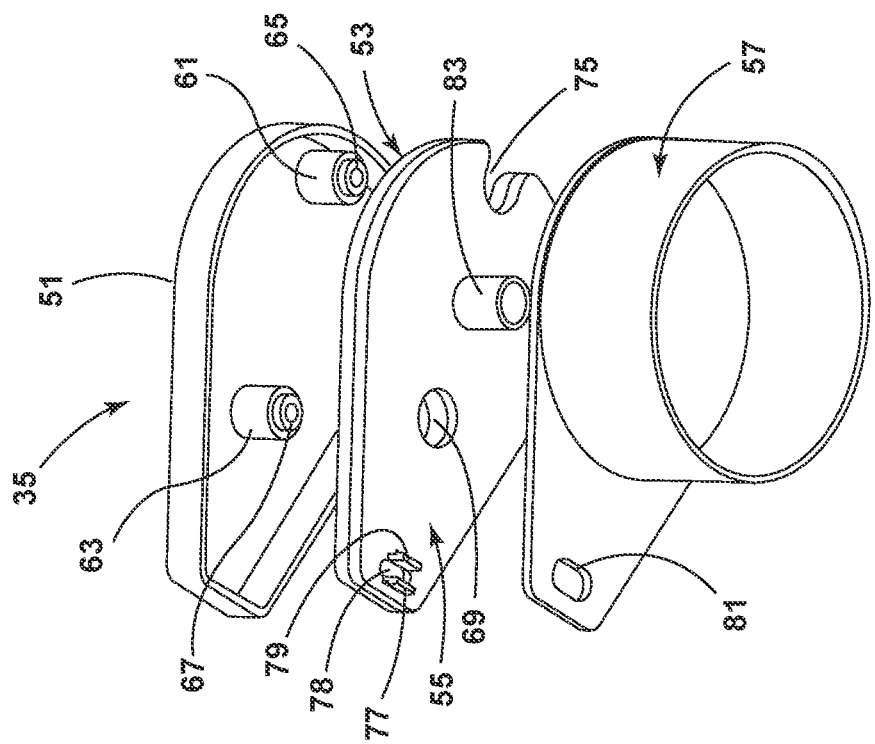
FIG. 9 is a bottom exploded perspective view of the pump top component of the apparatus of FIG. 1.
Figure 8:
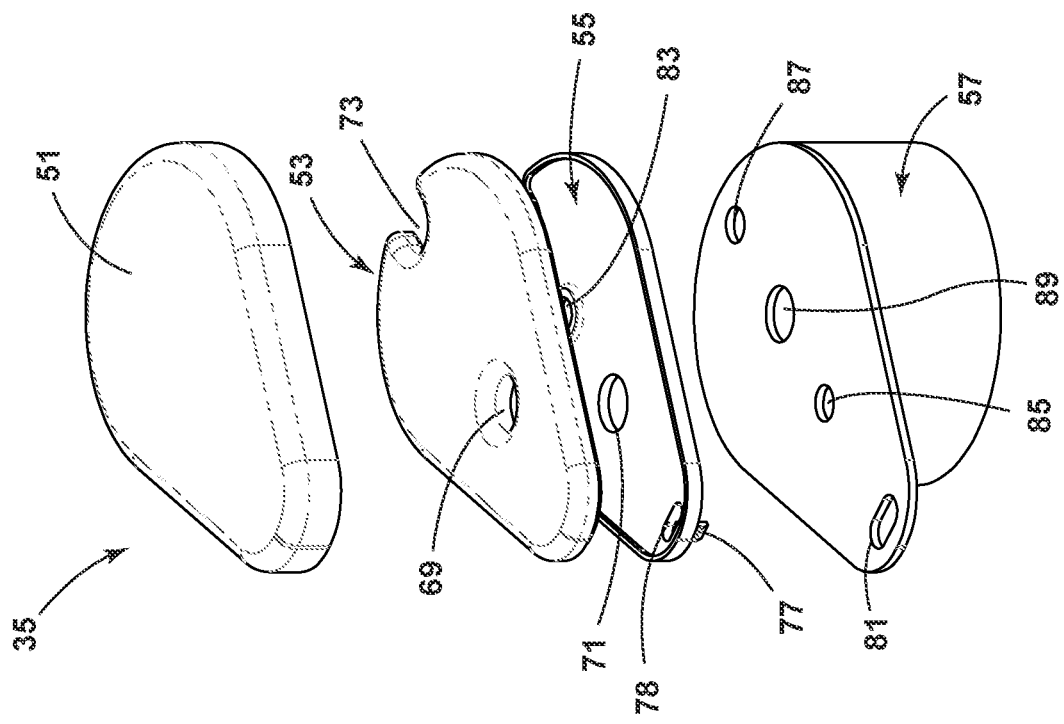
FIG. 8 is a top exploded perspective view of the pump top component of the apparatus of FIG. 1.
Figure 10:
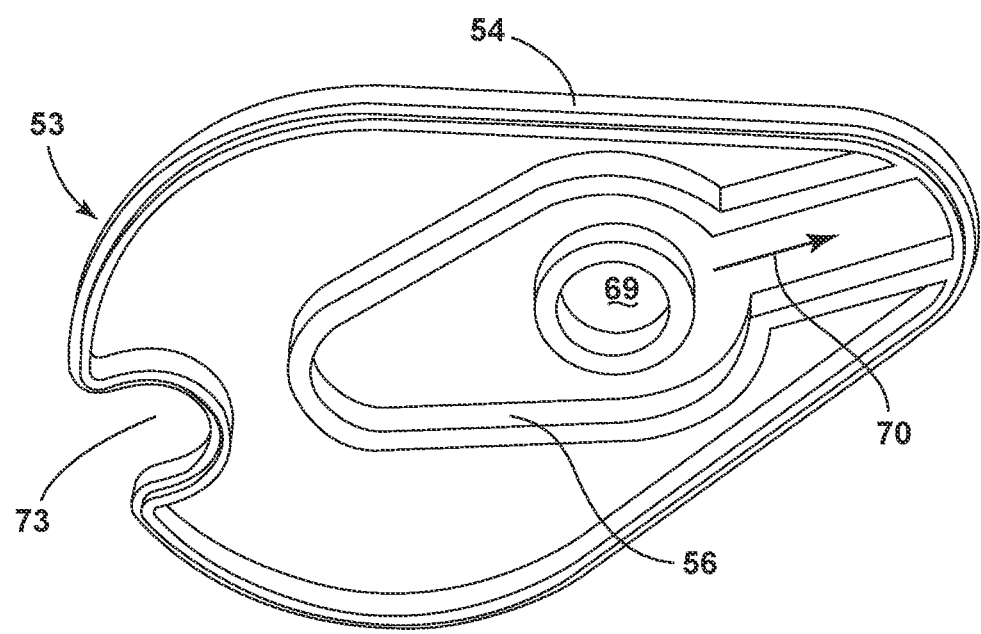
FIG. 10 is a perspective view of the bottom of an intermediate component of the top component of FIGS. 8 and 9.

As shown in FIGS. 8 and 9, the pump top 35 of the illustrative embodiment comprises four mating components 51, 53, 55, 57. The top component 51 includes two threaded bosses 61, 63 on its underside, each of which has a lipped feature 65, 67. Mating upper and lower intermediate components 53, 55 have mating openings 69, 71 and mating notches 73, 75 formed therein. The lower intermediate component 55 further has a liquid dispensing opening 78, a liquid receiving boss 83, and vertically depending tangs 77, 79 formed on either side of the liquid dispensing opening 78, which snap-fittingly engage a liquid dispensing opening 81 in the lower top component 57. As shown in FIG. 10, the upper intermediate component 53 has an outer rim 54 and an inner rim 56. The inner rim 56 defines a liquid flow path 70.

In assembly, the two intermediate component halves 53, 55 are fused together to create a hollow, sealed assembly which provides the path through which the stored liquid travels. The lower half 55 interfaces directly with the pump 41 whose stem 91 passes through hole 89 in the bottom half 57 and sealingly fits into boss 83 of the lower intermediate component 55. When the pump head 35 is manually depressed, liquid is expelled into the user's hand directly from the small opening 78 in the front of the lower intermediate component 55. The top and bottom components 51, 57 sandwich the sealed assembly 53, 55 to create an outer aesthetic appearance. In assembly, the guide pins, 45, 43, which, in one embodiment may comprise shoulder bolts, pass through the holes 85, 87 in the bottom component 57, through the holes 69, 71 and notches 75, 73 in each of the intermediate components 53, 55, and thread into the threaded bosses 61, 63 on the underside of the top component 51. In illustrative embodiments, the top and bottom components 51, 57 may attach via a snap press fit or induction seal. The shoulder bolts 45, 43 also provide a clamping force that squeezes top component 51 and bottom half 57 together.

In one embodiment, the bottom component 57 may be formed of metal such as stainless steel, for example, by a stamping procedure. The top 51 may also be formed of metal such as stainless steel with the threaded bosses 61, 63 welded thereto, while the two intermediate components are formed of a suitable plastic. These components 51, 53, 55, 57 may be fabricated from other materials by various procedures in other embodiments. In one embodiment, a press-fit engagement is formed between the open tip of the pump stem 91 and the boss on the lower intermediate component 55.

Figure 12:
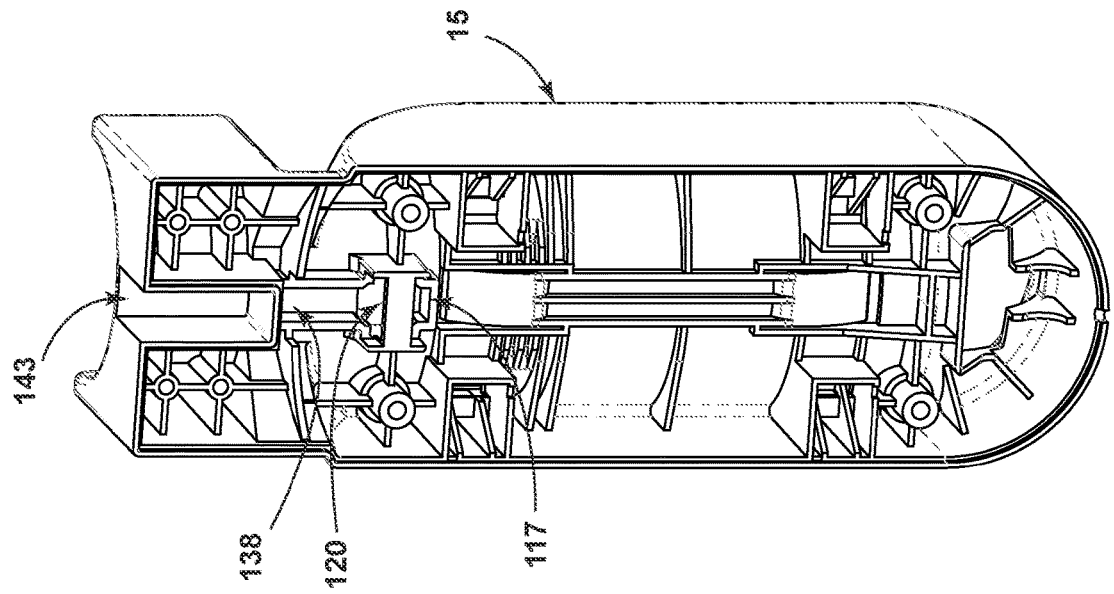
FIG. 12 a rear perspective view of the housing component of the apparatus of FIG. 1.
Figure 11:
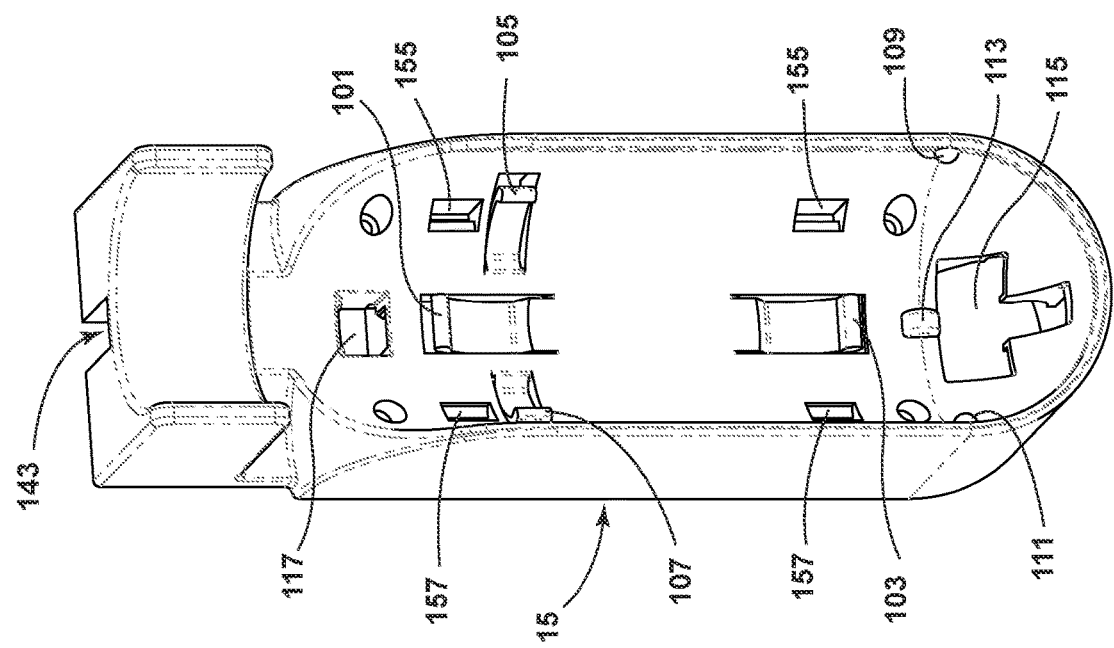
FIG. 11 is a front perspective view of the housing component of the apparatus of FIG. 1.

FIGS. 11 and 12 illustrates the housing 15 in further detail. As may be seen, the front facing interior surface of the housing 15 includes back surface positioning arms 101, 103, resilient side retaining arms 105, 107, side pivot bumps 109, 111, and a rear pivot bump 113. The rear surface further includes a tang receiving opening 115 and an aperture 117 through which the hook 40 of the closure 37 passes.

Figure 14:
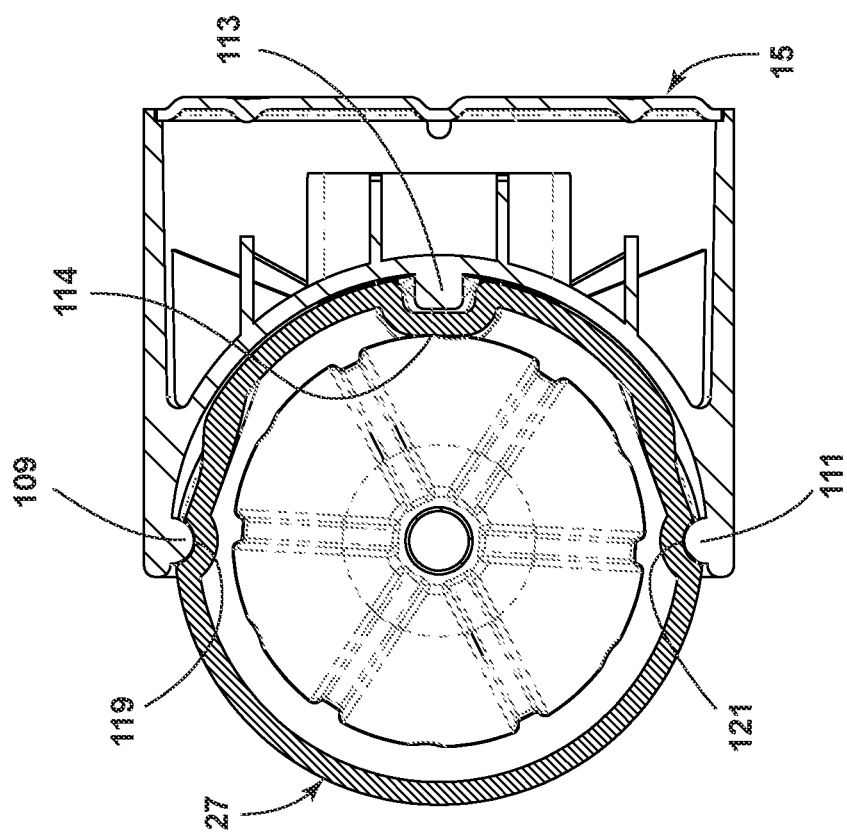
FIG. 14 is a sectional view taken at 14-14 of FIG. 1.
Figure 13:
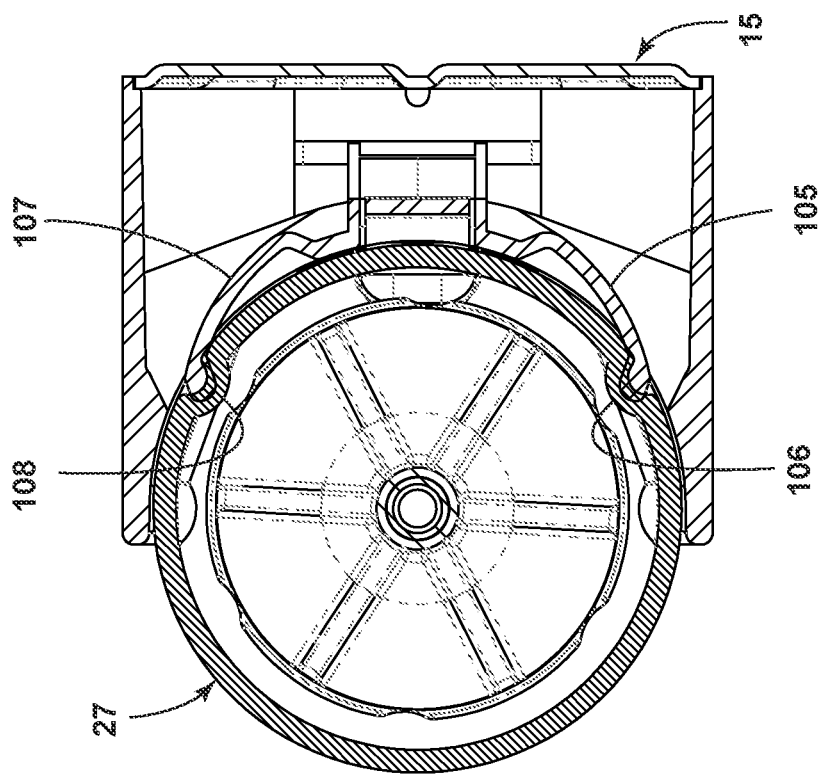
FIG. 13 is a sectional view taken at 13-13 of FIG. 1.

As may be seen in FIGS. 13 and 14, the side pivot bumps 109, 111 fit into respective pivot notches 119, 121 formed on the lower sides of the canister 27, and the rear pivot bump 113 interfaces with a suitably shaped contour 114 on the lower rear surface of the canister 27 to provide for pivotal movement of the canister 27 about a horizontal axis defined by the two side bumps 109, 111. In one embodiment, guideways, e.g. 110 (FIG. 5) facilitate passage of the pivot bumps 109, 111 into their respective notches 119, 121.

As may be seen in FIG. 13, the ends of the resilient side arms 105, 107 snap into respective indentations 106, 108 in the canister 27 in order to position and retain the canister 27 in an installed position. FIG. 14 illustrates how the resilient positioning arms 101, 103 support the back surface of the canister 27, as well as how bottom tang 31 fits into the tang receiving opening 115.

The manner in which the bottom tang 31 fits into the tang receiving opening 115 is further illustrated in FIGS. 19 and 20 where the canister 27 is shown in its vertical upright position. Here it may be seen that the tang 31 is cylindrical and is positioned to pivot in a mating circular arc 116 formed in the housing 15.

Figure 15:
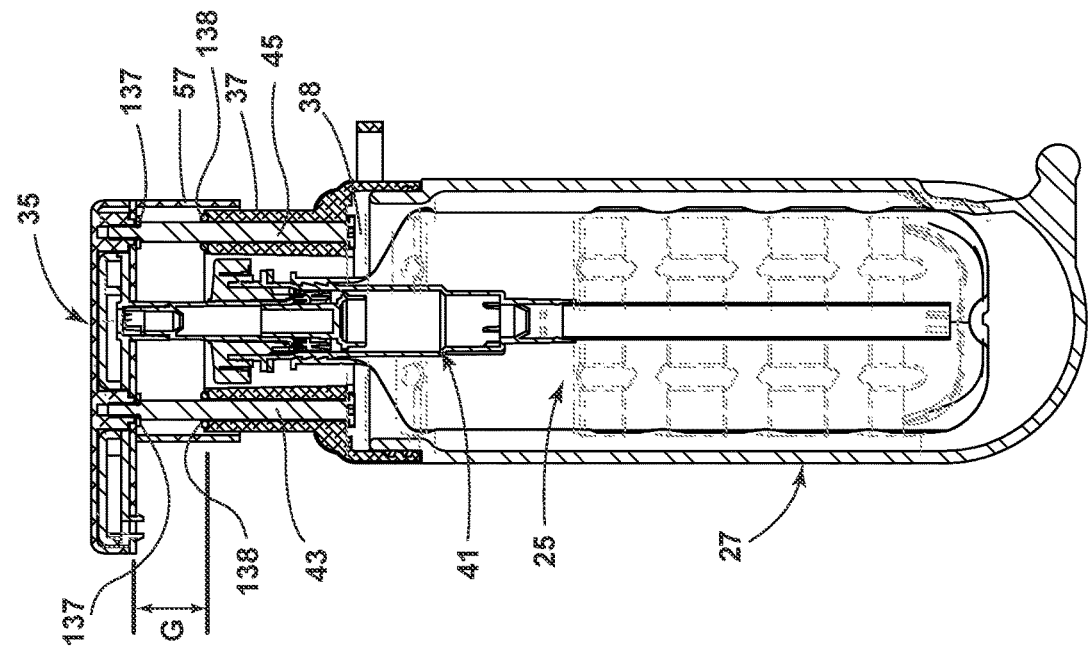
FIGS. 15 and 16 are side sectional views taken at 15-15 of FIG. 2.

In assembly, the canister 27 is installed into the housing 15 at the same angle as the service position—roughly 20 degrees—allowing the tang 31 to pass through the housing opening 115. Once the pivot bumps/notches 109, 111/119, 121 are engaged, and the canister 27 is rotated back to the vertical position of FIG. 16, the plastic housing 15 prevents the canister 27 from being removed. Thus, the locking pin 14 described further below and this feature work in combination to create two retention points spread as far apart as possible (top and bottom), preventing the canister 27 from being pulled off or out of the housing 15. In one embodiment, the positioning arms 101, 103, 105, 107 (FIG. 15) also provide "preload to the dispenser canister 27 when in the vertically docked position.

Figure 16:
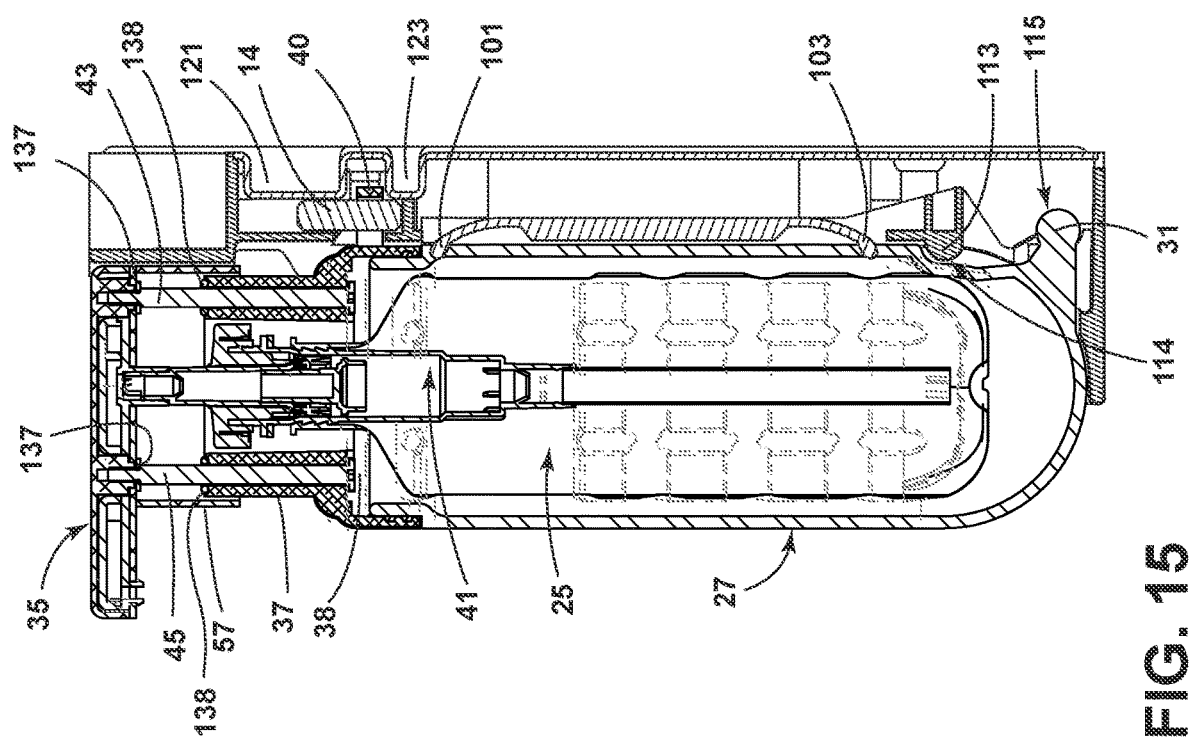
Figure 18:
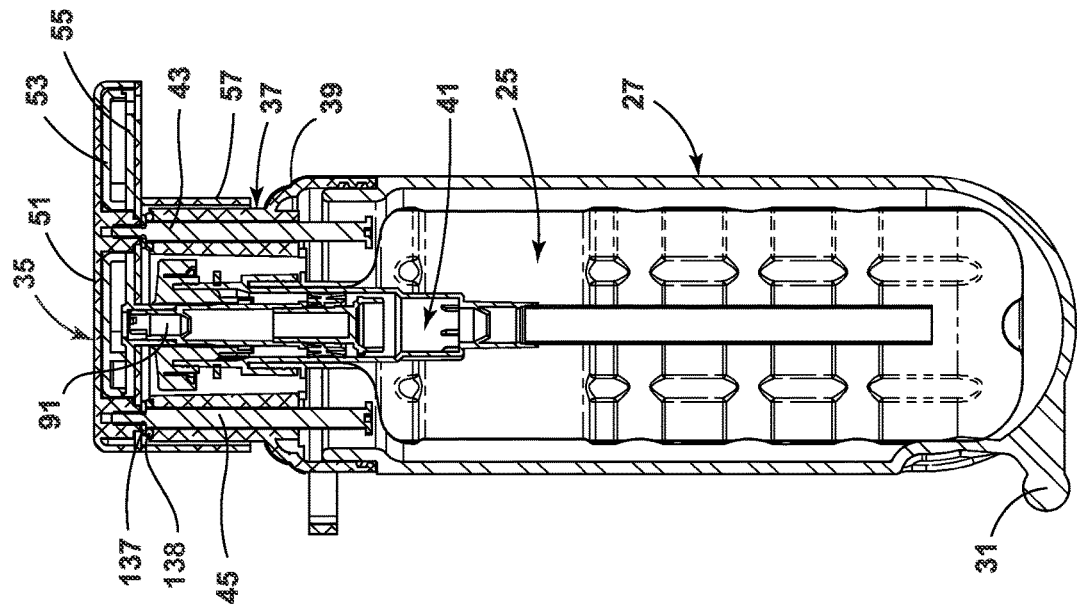
FIG. 18 is a side sectional view of the apparatus of FIG. 17 showing the pump head of FIG. 17 in a manually depressed position.
Figure 17:
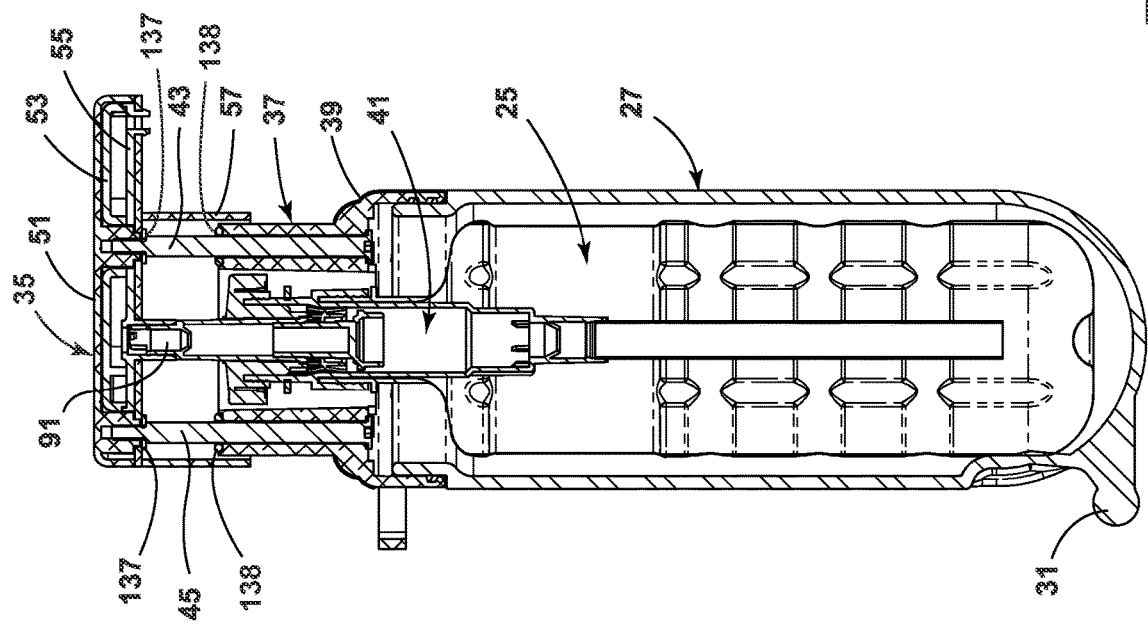
FIG. 17 is a side sectional view of an illustrative liquid dispensing unit showing the pump head of the apparatus in an extended position.
Figure 23:
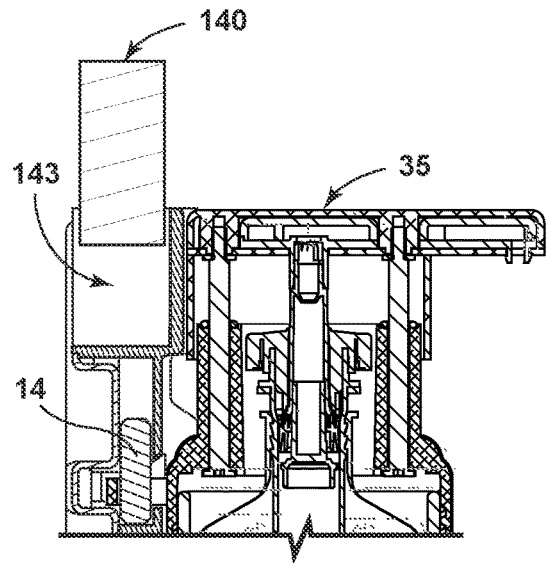
FIG. 23 is a partial side sectional view illustrating a mechanism for locking the liquid dispensing unit of the illustrative embodiment in position.
Figure 24:
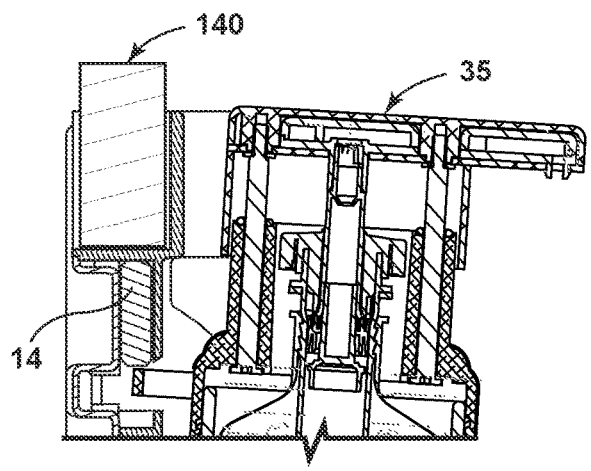
FIG. 24 is a second side sectional view further illustrating the locking mechanism of FIG. 23.
Figure 25:
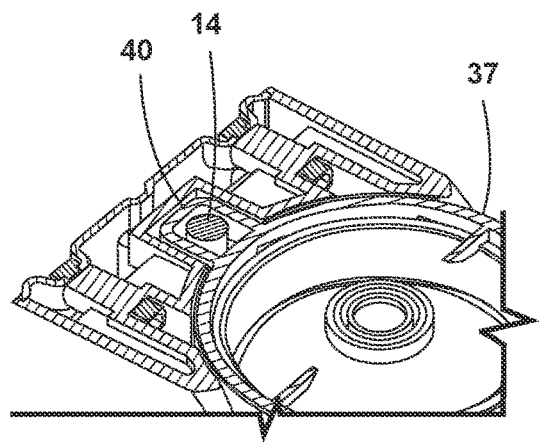
FIG. 25 is a partial sectional perspective view further illustrating the locking mechanism of FIG. 23.
Figure 26:
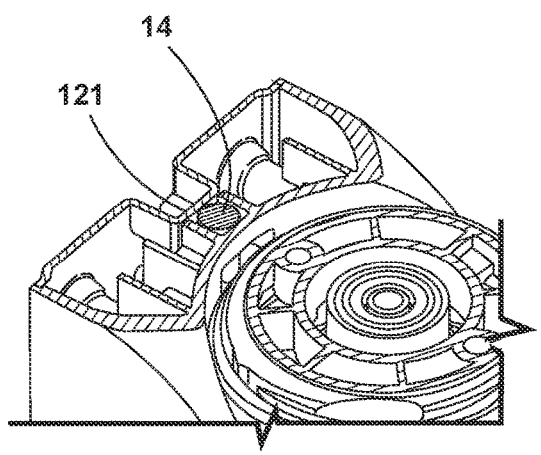
FIG. 26 is a second partial sectional view further illustrating the locking mechanism of FIG. 23.
Figure 28:
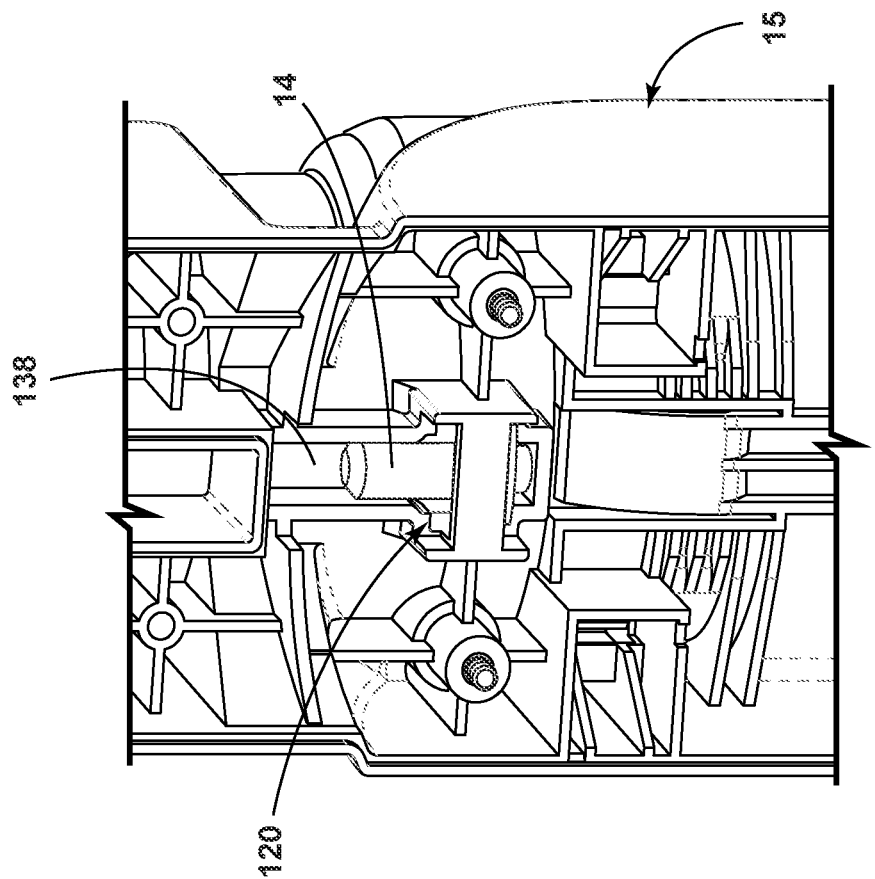
FIGS. 27 and 28 are rear perspective views of the housing component illustrating positioning of the magnetic locking pin of the locking mechanism.
Figure 27:
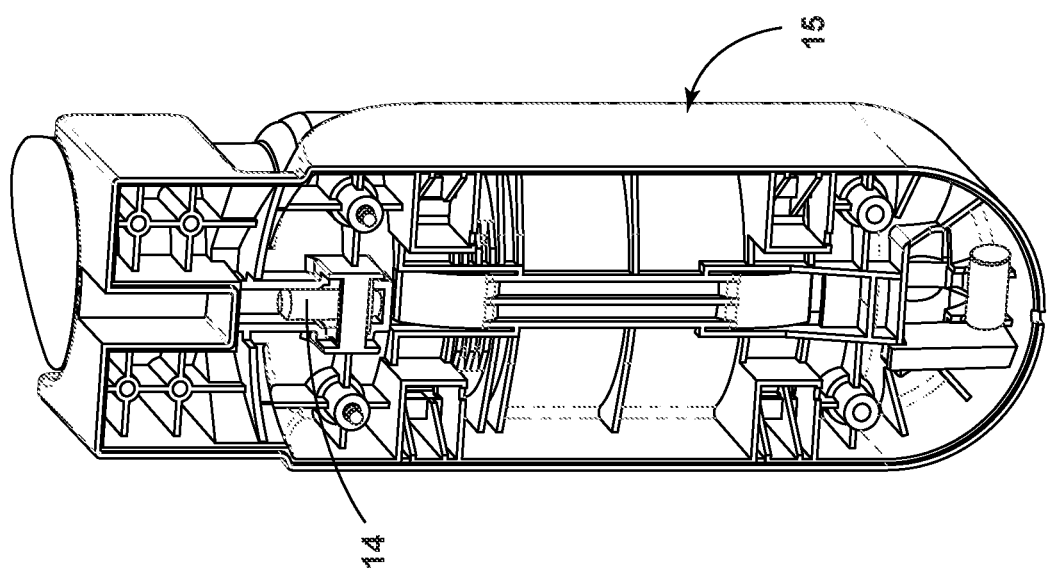
Figure 35:
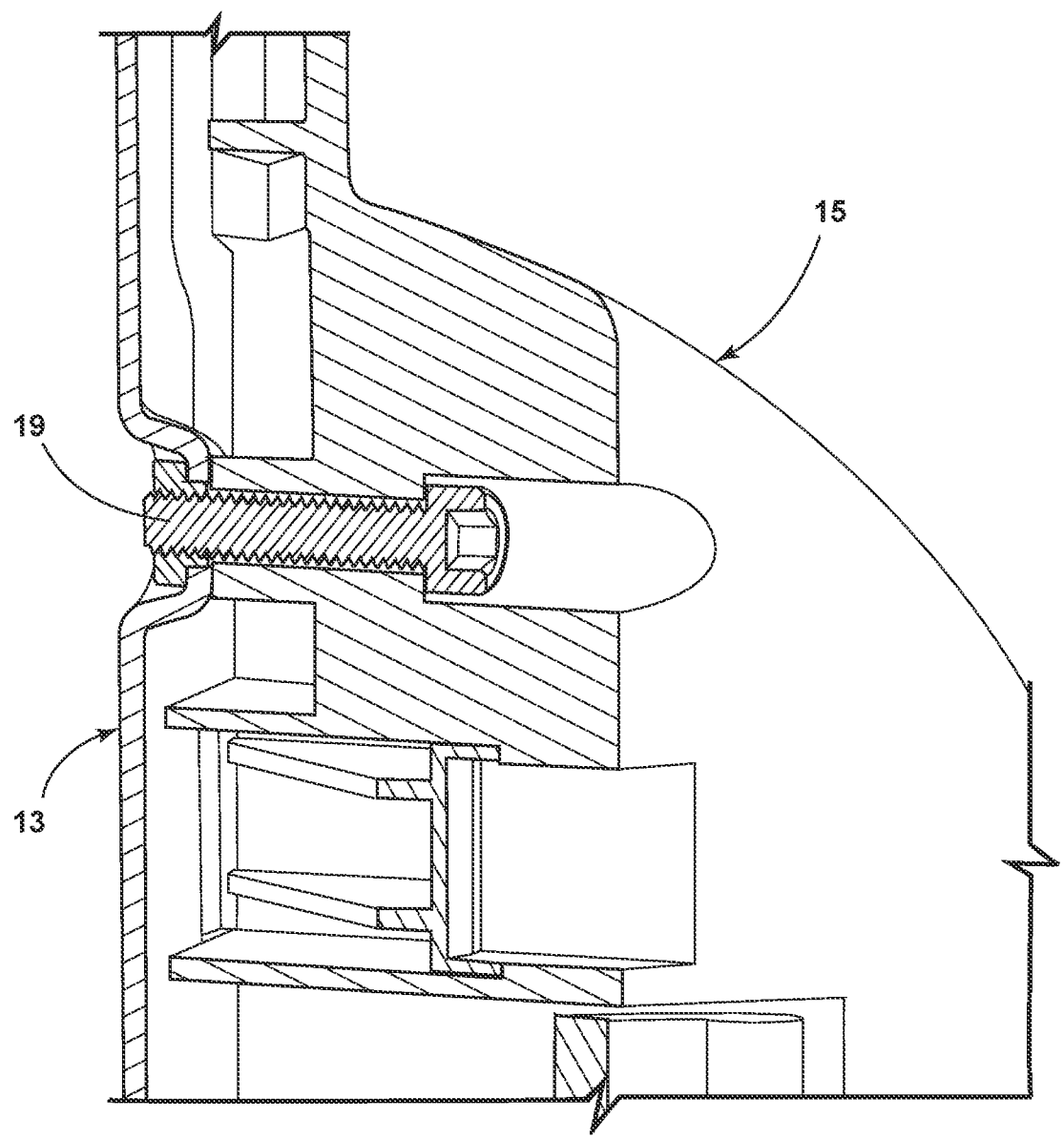
FIG. 35 is a partial side sectional view illustrating attachment of the back plate to the housing in an illustrative apparatus according to FIG. 1.

As may be further seen in FIGS. 15-18, the guide pins 43, 45 extend through respective bores of the closure 37. The pump 41 does not interface directly with the guide pins 43, 45, but rather attaches to the closure 37 via two dowel pins 131, 133 and cooperating ¼ turn style tracks 135 located on opposite sides of the pump 41, as illustrated in FIGS. 21 and 22. Thus, in assembly according to one embodiment, the guide pins 43, 45 are installed to mount the pump head 35 to the closure 37. The user then slides the cartridge assembly comprising the cartridge 25 and pump 41 into the closure 37 from below, engages the tracks 135 with the dowel pins 131, 133, and rotates that assembly some distance (for example, a ¼ turn or 45 degrees or some other selected angle) to lock it in place. This action pushes the top of the stem 91 of the pump 41 (where liquid is expelled) into the receiving underside of the pump head 35. The spring bias of the pump 41 holds the pump head 35 in its extended position as shown in FIG. 16. O-rings 137, 138 provide a cushioned stop when the travel distance "G" is closed during pumping.

FIGS. 15 and 23-28 further illustrates the locking or latching mechanism of the illustrative embodiment. According to this embodiment, the liquid dispenser unit 17 is inserted into the housing 15 and pivoted into the installed position shown in FIG. 14. The ferromagnetic locking pin 14 is then inserted down through an opening 138 into a cavity 120 (See FIG. 12, 28) in the rear of the housing 15 and through the opening in the hook 40 of the closure 37. The back plate 13 is then attached to the housing 15 to encase the locking pin 14. In one embodiment the pin 14 may be round and the cavity 120 square in cross-section.

According to the illustrative embodiment, the pin 14 is permanently encased inside the assembled components with the rear metal back plate portions 121, 123 (FIG. 15) acting as a rear cover, trapping the pin 14 in the plastic housing 15, such that only vertical motion of the pin 14 is allowed. Under its own weight, the pin 14 falls down through the hook 40 and "locks" the device. To unlock the device, a magnet key 140 (FIG. 19, 20) is dropped into a deep channel 143 in the housing 15 to get as close to the pin 14 as possible, so as to pull the pin 14 up against gravity. In this position, the hook 40 on the closure 37 is now free to move, allowing canister 27 to rotate into the service position (FIG. 3) where the cartridge 25 can be replaced or the liquid dispenser unit 17 removed from the housing 15.

In the illustrative embodiment, the canister 27 is held in this position by the flexure arms 105, 107, but the retention force of those components can be easily overcome by manually attempting to rotate the canister 27 downward. The locking pin 14 prevents such rotation. Thus, the locking pin 14 prevents someone from both accessing the "service" position and removing the canister 27.

Thus, according to an illustrative procedure, once the liquid dispenser 17 is pivoted to the service position of FIG. 3, the closure 37 and pump head 35 are ¼-turned to separate the closure 37 from the canister 27. The attached spent cartridge (or reservoir) 25 and integrated pump 41 are ¼-turned to separate them from the closure 37. A fresh full cartridge 25 with integrated pump 41 is then inserted from the bottom side into the closure 37 and ¼-turned to fasten the assembly into position. The closure 37 with pump head 35, pump 41 and full cartridge 25 are then inserted into the top of the canister 27. The closure 37 is then seated on the rim of the canister 27 and twisted ¼-turn to fasten the closure 37, pump top 35, pump 41 and full cartridge 25 into the canister 27. The liquid dispenser unit 17 is then pivoted back to the fully vertical position, and the magnetic key 140 is removed allowing the locking pin 14 to drop into the locked position, thus securing the liquid dispenser 17 in locked position in the housing 15. In an alternate embodiment, the same opening and closing procedures are employed. However, there is no cartridge 25 or other reservoir present. In such and embodiment, the canister 27 acts as a reservoir and is directly bulk filled by pouring the liquid to be dispensed from a fill bottle into the canister 27. The pump 41 may be reused or replaced.

The illustrative embodiment further provides a leveraged removal feature, as illustrated in FIGS. 29-31. The track surface 151 formed on the lower rear surface of the canister 27 and the bump out 113 on the plastic housing 15 creates a "stop" at the ~20-degree service position (FIG. 30). But if the user continues to pull the canister 27 downward past that position, the force created at this point on the two spherical bump features 109, 111 creating the canister's axis of rotation causes the canister 27 to pop out of that joint (FIG. 31), allowing the entire liquid dispensing unit 17 to be removed from housing/back plate assembly. In another embodiment, a pair of bumps offset on either side of the central position of bump 113 and cooperating grooves formed in the canister 27 may be employed to provide the removal feature.

FIGS. 32-34 illustrate a resilient clip 153 configured to join or connect two adjacent housings 15. To connect the two housings 15 shown in FIG. 34, the clip 153 is spread apart from its unbiased state shown in FIG. 32 to take on the shape shown in FIG. 33. When so spread apart, the clip 153 can be installed as shown in FIG. 34 to engage respective undercuts 155, 157 formed in the housing 15. These undercuts 155, 157 are further illustrated in FIG. 11, which shows an upper pair of undercuts 155, 157 and the lower pair 155, 157 shown in FIG. 34. Thus, in an illustrative embodiment, clips 153 are installed in upper and lower positions on the housing 15.

According to an illustrative first installation embodiment, the liquid dispenser apparatus 11 is installed on a stone, ceramic, or plastic surface. In the first embodiment, the installation surface must be thoroughly cleaned of any grease, dirt, soap or sealer and then thoroughly dried. The housing 15 is attached to the back plate 13 with screw fasteners 19. If there are two or more dispensers 11 to be mounted together, the housings 15 are then joined together, side-by-side, using clips 153 shown in FIGS. 32-34. Each attached back plate 13 will have bonding tape affixed to its metal surface. The backing on the bonding tape is then removed from each metal back plate 13 exposing a sticky surface. The single or ganged back plates 13 with housings 15 are then adhered by pressing to the installation surface. The housings 15 are then removed from the adhered metal back plates 13, and added pressure (20 psi) is applied to each back plate 13 for 20-seconds. Optionally, a bead of silicone sealant may be run down the opposite vertical edges of the back plate 13. The locking pin(s) 14 are placed in the housing recesses 138. The housing(s) 15 are then reattached to the back plate(s) with screw fasteners 19. The liquid dispenser 17 is snap fit into each housing 15 at the service position. The magnetic key 140 is inserted into channel 143, and each liquid dispenser 17 is rotated to its seated vertical position. The magnetic key 140 is removed, and the installation is complete.

According to an illustrative second installation embodiment, the liquid dispenser apparatus 11 is installed on a hollow wall surface. In the second embodiment the installation surface is cleaned of any dirt or residue. The housing 15 is attached to the back plate 13 with screw fasteners 19. If there are two or more dispensers 11 to be mounted together, the housings 15 are then joined together, side-by-side, using clips 153 shown in FIGS. 32-34. Each attached back plate 13 will have bonding tape affixed to the metal surface. A small amount of the backing on the bonding tape is removed exposing a small sticky area. The single or ganged back plates 13 with housings 15 are then adhered by pressing to the installation surface. The housings 15 are then removed from the adhered metal back plates 13, and hollow wall anchors and their associated screw fasteners are installed through the metal back plates 13. Optionally, a bead of silicone sealant may be run down the opposite vertical edges of the back plate 13. The locking pin(s) 14 are placed in the housing recesses 138. The housing(s) 15 are then reattached to the back plate(s) 13 with screw fasteners 19. The liquid dispenser unit 17 is snap fit into each housing 15 at the service position. The magnetic key 140 is inserted into channel 143, and each liquid dispenser unit 17 is rotated to its seated vertical position. The magnetic key 140 is removed, and the installation is complete.

According to an illustrative third installation embodiment, the liquid dispenser apparatus 11 is installed on a mirror. In the third embodiment, the installation surface must be thoroughly cleaned of any grease, dirt, soap or sealer; and then thoroughly dried. The housing 15 is attached to the back plate 13 with screw fasteners 19. If there are two or more dispensers 11 to be mounted together, the housings 15 are then joined together, side-by-side, using clips 153 shown in FIGS. 32-34. Each attached back plate 13 will have bonding tape affixed to the metal surface. The backing on the bonding tape is then removed from each metal back plate 13 exposing a sticky surface. The single or ganged back plates 13 with housings 15 are then adhered by pressing to the installation surface. The housings 15 are then removed from the adhered metal back plates 13, and added pressure (20 psi) is applied to each back plate 13 for 20-seconds. Optionally, a bead of silicone sealant may be run down the opposite vertical edges of the back plate 13. The locking pin(s) 14 are placed in the housing recesses 138. The housing(s) 15 are then reattached to the back plate(s) 13 with screw fasteners 19. A liquid dispenser unit 17 is snap fit into each housing 15 at the service position. The magnetic key 140 is inserted into channel 143, and each liquid dispenser unit 17 is rotated to its seated vertical position. The magnetic key 140 is removed, and the installation is complete.

Figure 37:
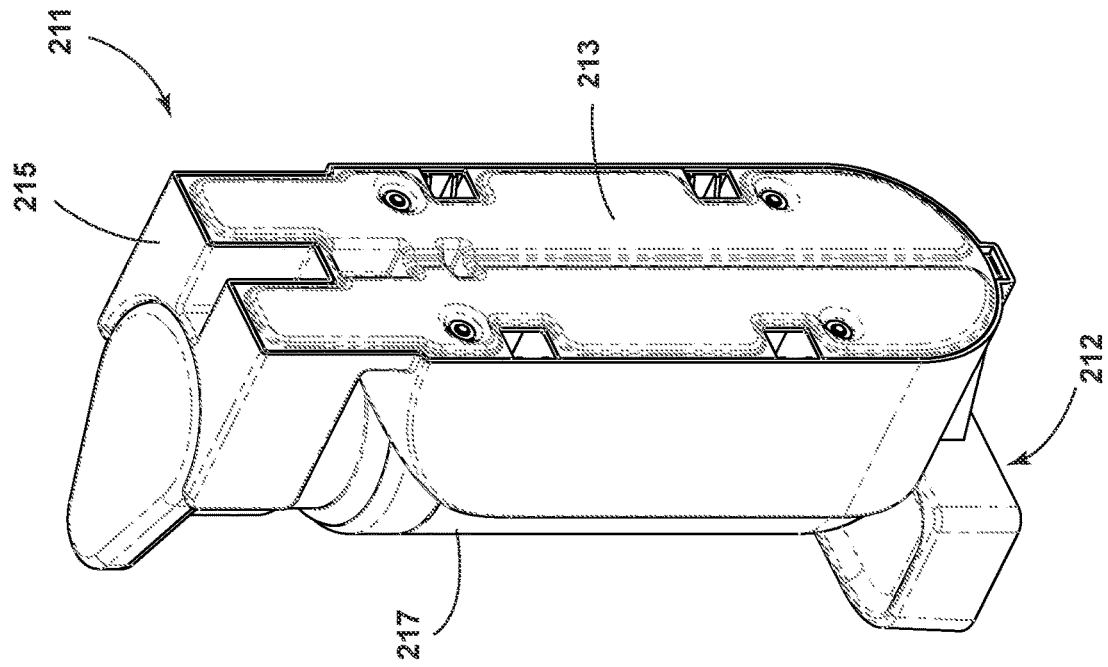
FIG. 37 is a rear perspective view of the apparatus of FIG. 36.
Figure 36:
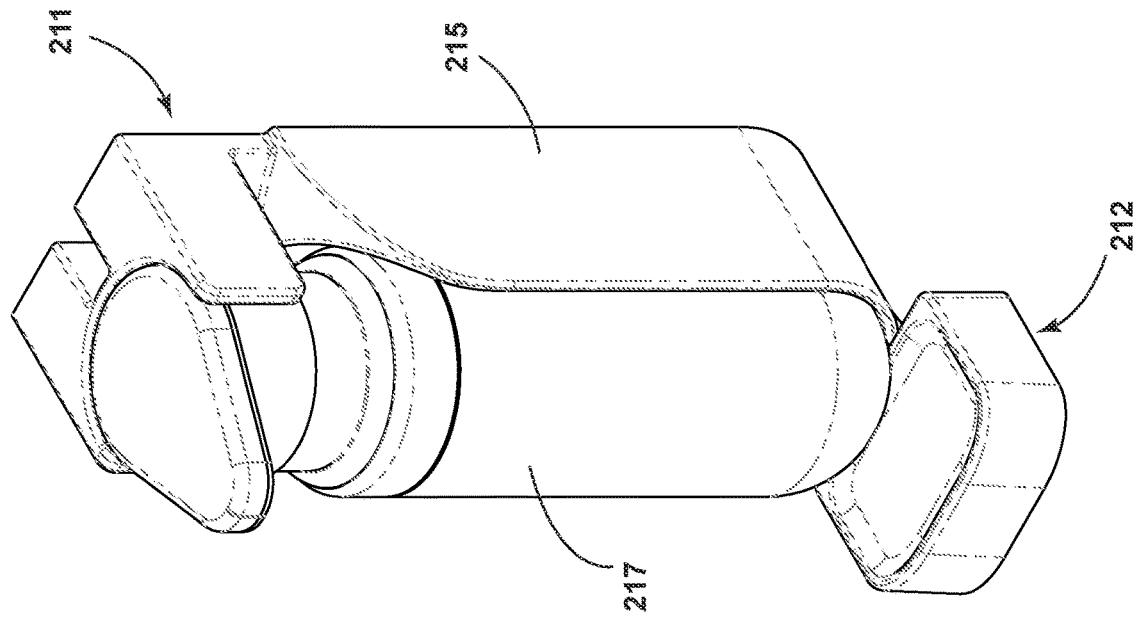
FIG. 36 is a front perspective view of a second illustrative embodiment of a liquid dispenser apparatus.
Figure 38:
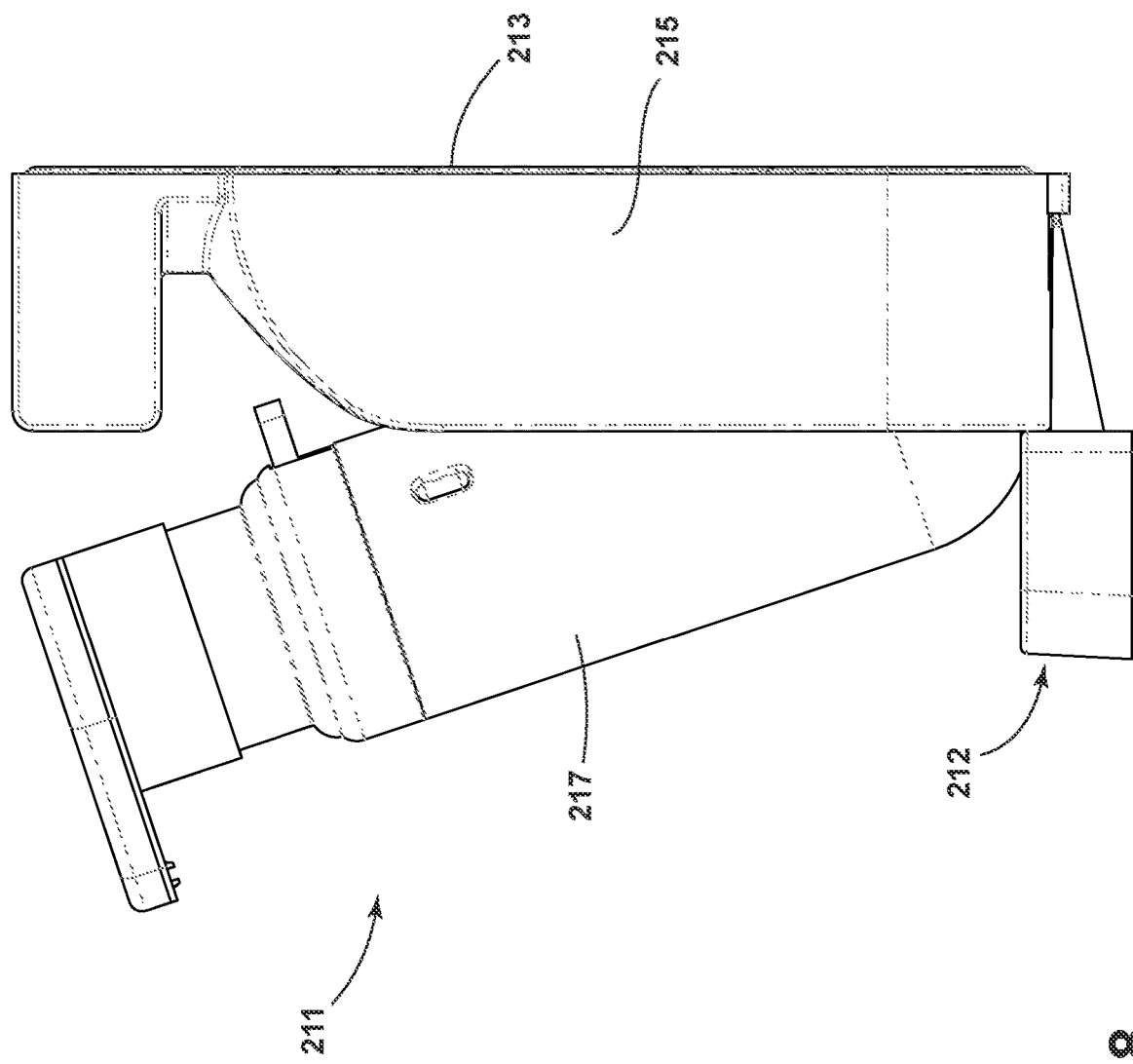
FIG. 38 is a side view of the apparatus of FIG. 1 in a service position.

FIGS. 36-38 depict a second illustrative liquid dispenser embodiment 211 featuring a drip tray 212, which, in one embodiment, may be a plastic molded part. The dispenser apparatus 211 further includes a back plate 213, a housing 215, and a liquid dispenser unit 217.

Figure 40:
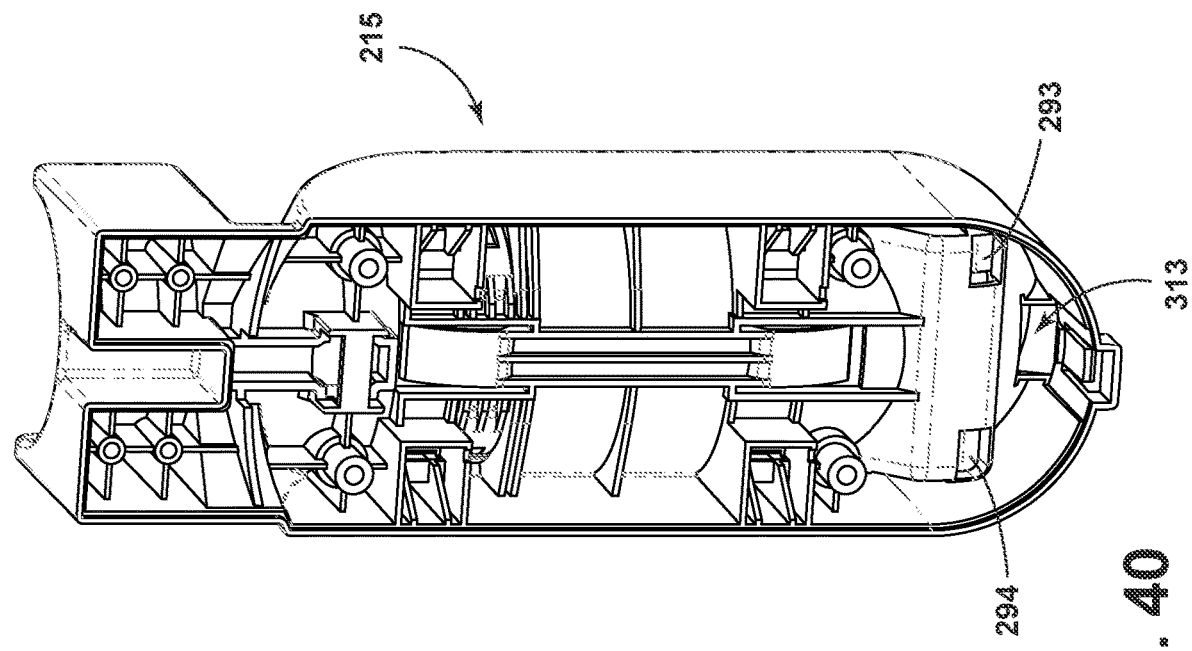
FIG. 40 is a rear perspective view of the housing of FIG. 39.
Figure 39:
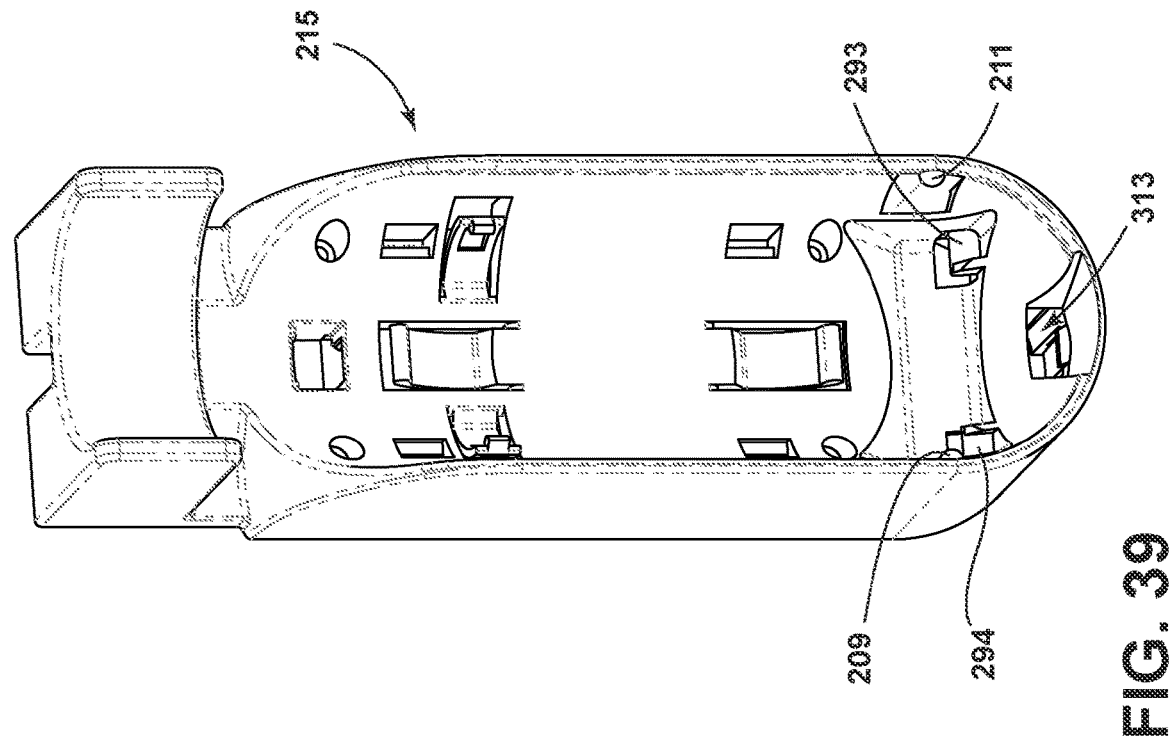
FIG. 39 is a front view of a housing component of the apparatus of FIG. 1
Figure 43:
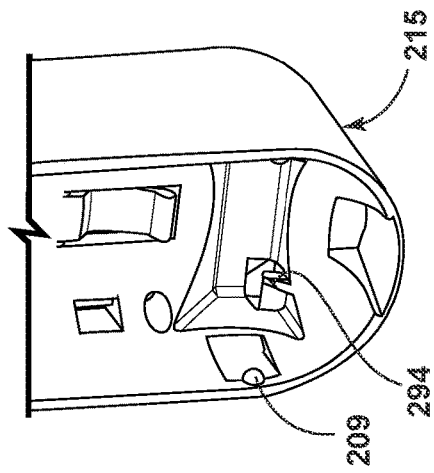
FIG. 43 is a partial front perspective view of a housing component for implementing the second illustrative canister catch/release mechanism.
Figure 42:
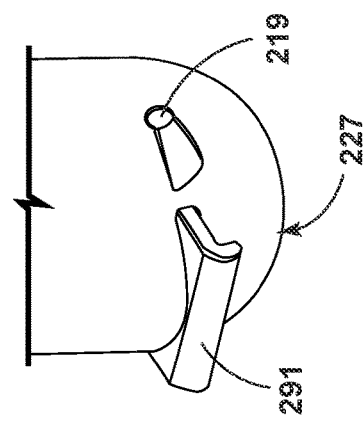
FIG. 42 is a partial rear perspective view of the mechanism of the apparatus of FIG. 41.
Figure 41:
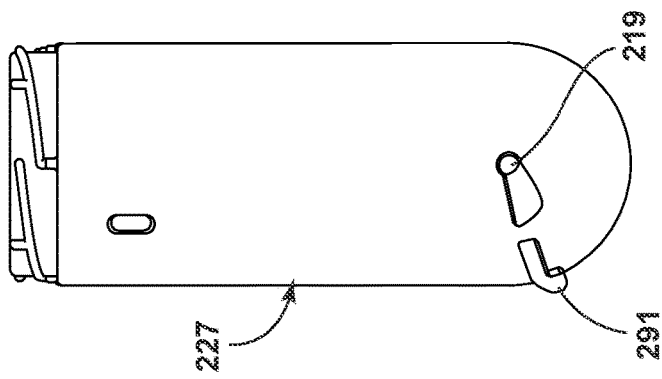
FIG. 41 is a second illustrative embodiment of a canister latch/release mechanism.
Figure 45:
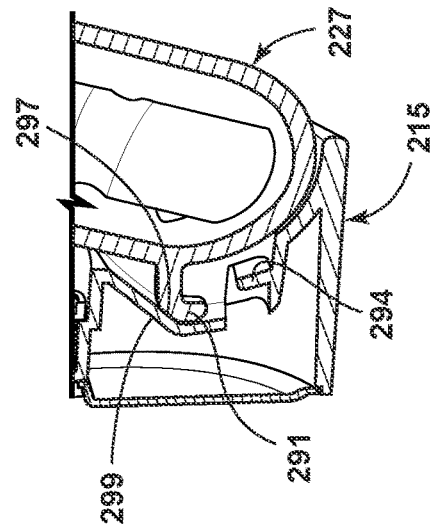
FIGS. 44 and 45 are partial side sectional views illustrating operation of canister catch/release mechanism.

The housing 215 is illustrated in further detail in FIGS. 39 and 40. It may be constructed similarly to the housing 15 disclosed in FIGS. 11 and 12 but includes structural differences in the lower portion such as respective latches 293, 294, which form part of a second canister attachment embodiment and an opening 313, which facilitates attachment of the drip tray 21 as discussed in further detail below.

Figure 44:
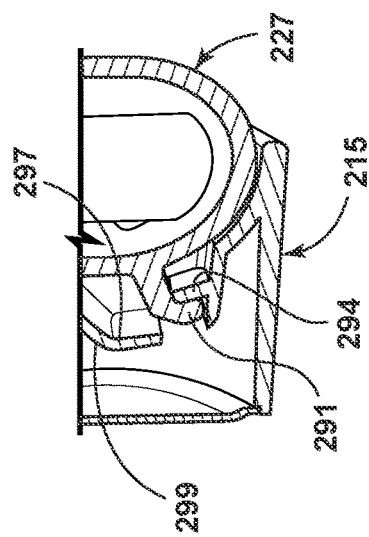

A second illustrative embodiment of a canister latch/release mechanism is shown in FIGS. 41-46. The second illustrative embodiment employs an attachment member comprising a wide, lower profile hook 291 located on the back of the canister 227. As in earlier described embodiments, the spherical feature, e.g. 209 (FIG. 43), and notches, e.g. 219 (FIG. 42), snap together to create an axis of rotation. As the canister 227 is rotated into a vertical position, the hook 291 on the canister engages the first and second latches 293, 295 formed on opposite sides of the plastic housing 215 (FIG. 44).

To remove the canister 227, the canister 227 is rotated forward until it is approximately 20 degrees off vertical. In this position, it rests under its own weight. By physically pulling the canister 227 further down—like a lever—a shoulder surface 297 of the hook 291 reacts with the angled housing surface 299 to disengage the canister 227 from the spherical joints 209, 211 and allow it to pop out of the housing 215.

Figure 46:
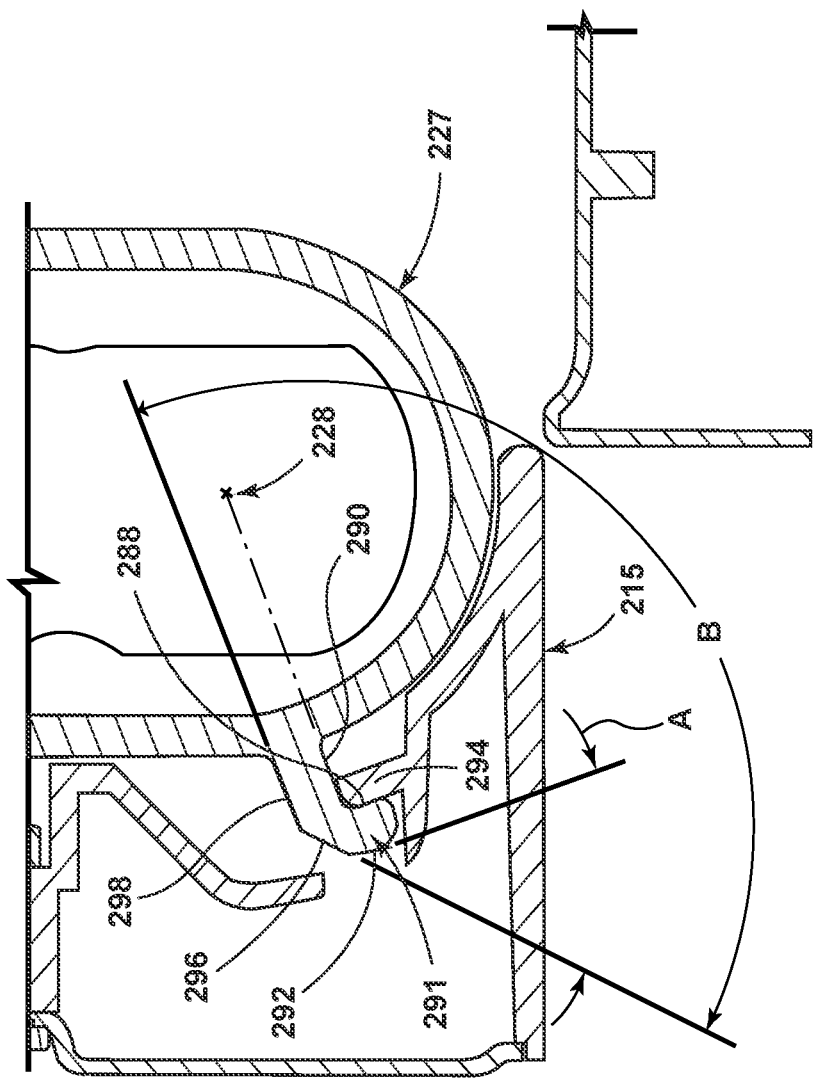
FIG. 46 is an enlarged side sectional view of the mechanism of FIG. 41.

FIG. 46 illustrates further details of one embodiment of the hook 291, which has five sides 288, 290, 292, 296 and 298. In one embodiment, the angle "A" between sides 292 and 296 may be 46.50 degrees, while the angle "B" between sides 292 and 298 may be 138.00 degrees. Sides 288 and 290 are perpendicular to one another. Side 290 is a planar surface that intersects the axis of rotation 228 of the canister 227 as shown by a dashed line. Thus, side 290 is perpendicular to the canister 227 at their intersection point. The just described dimensioning and angular relationships may vary in various embodiments.

Figure 47:
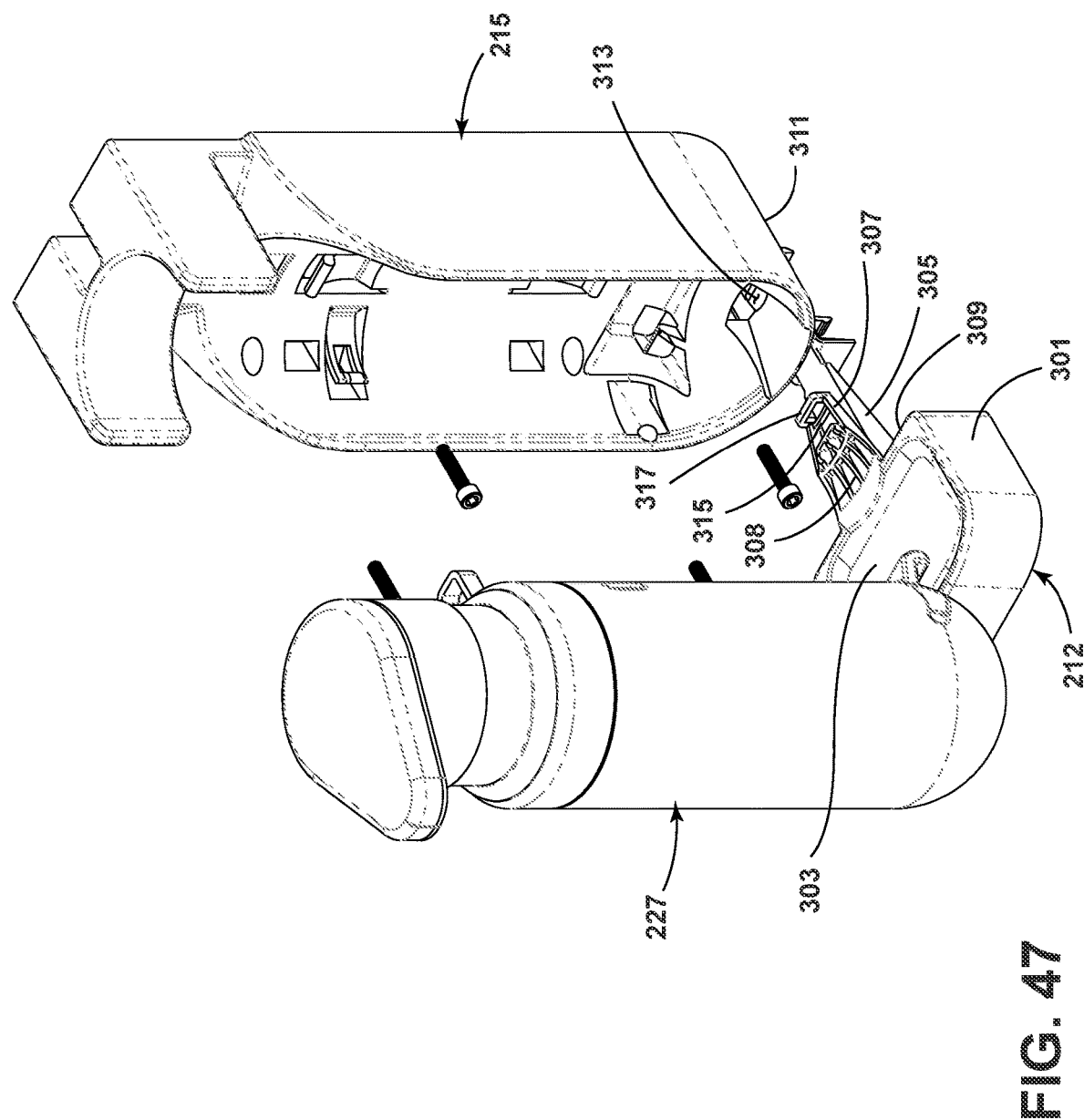
FIG. 47 is an exploded perspective view of the apparatus of FIG. 36.
Figure 49:
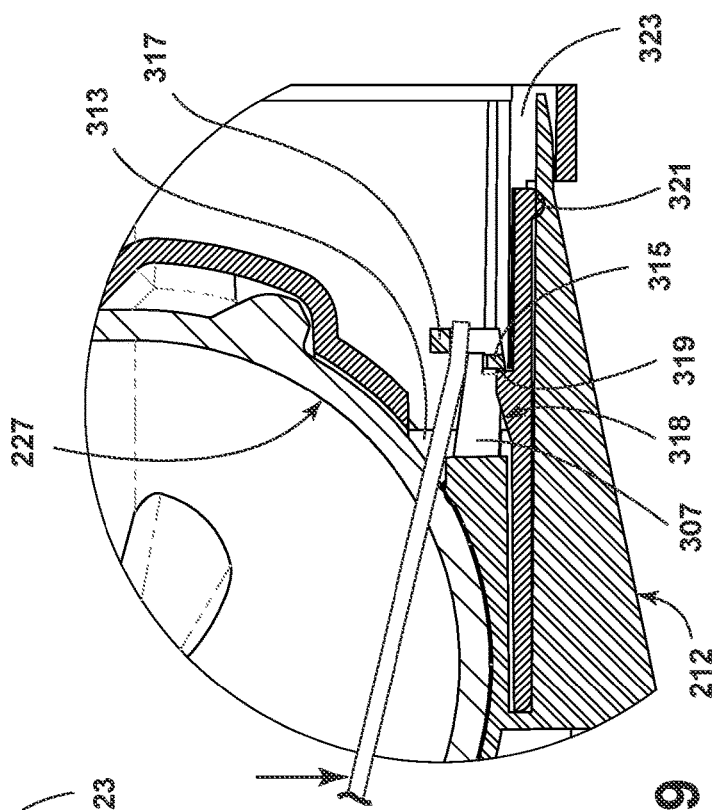
FIGS. 48 and 49 are partial side views further illustrating interference preload and snap insertion removal features of the drip tray and canister components of the apparatus of FIG. 36.
Figure 48:
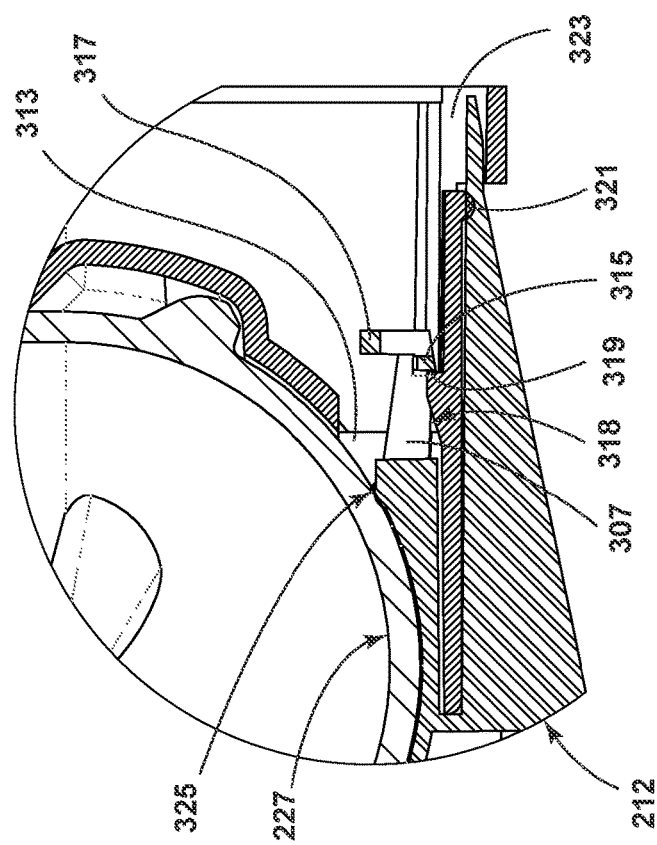
Figure 50:
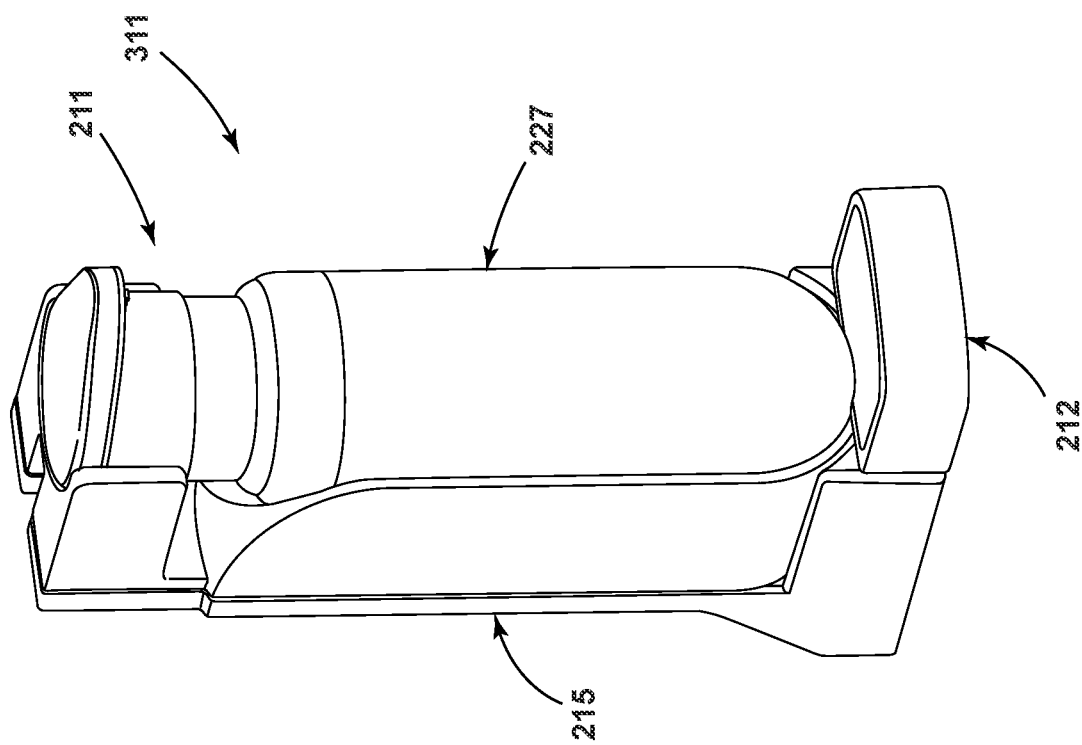
FIG. 50 is a front perspective view of a table mount liquid dispenser embodiment.
Figure 51:
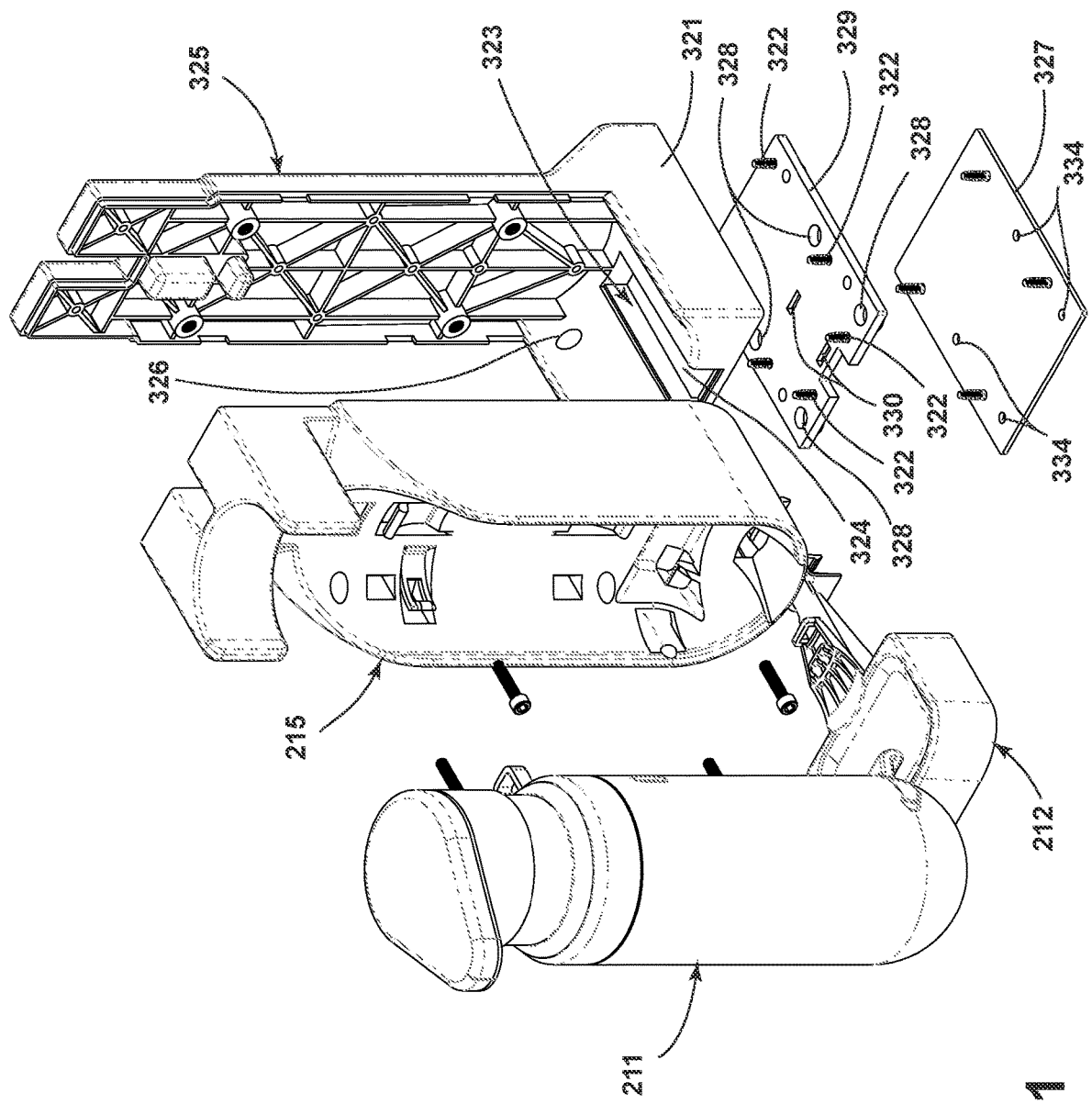
FIG. 51 is an exploded perspective view of the dispenser embodiment of FIG. 50.
Figure 53:
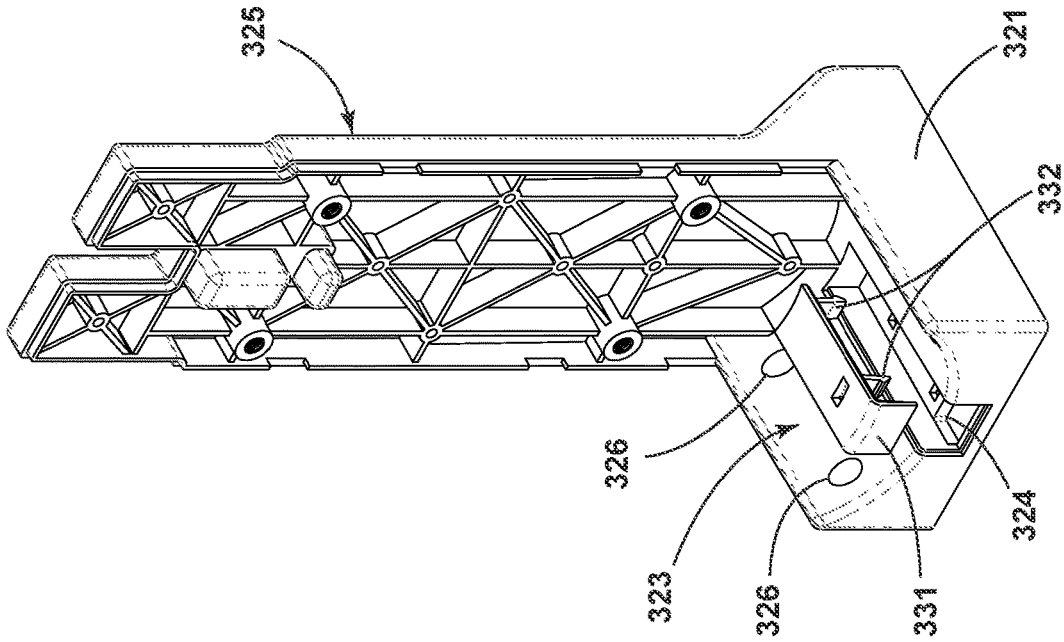
FIG. 53 is a second perspective view of the apparatus of FIG. 52.
Figure 52:
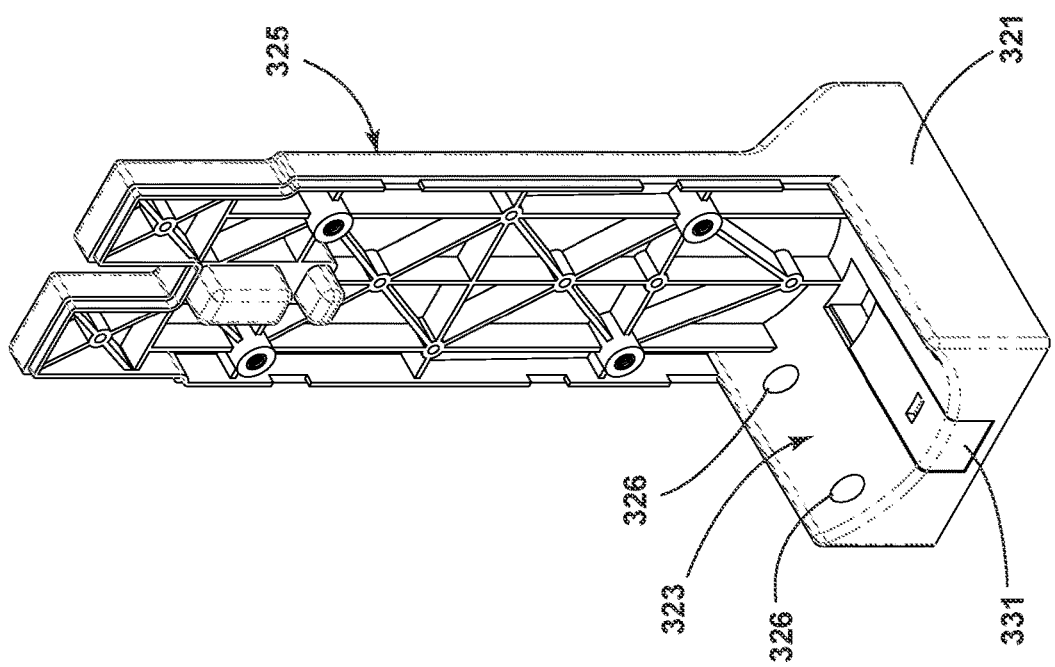
FIG. 52 is a perspective view of apparatus for mounting the housing of the embodiment of FIG. 50 to a tabletop.

As shown in FIGS. 47-49, the illustrative drip tray 212 includes a generally rectangular drip collection receptacle 301 having a central depression 303 shaped to collect dripped liquid. Upper and lower tongues 305, 307 extend horizontally from the rear surface 309 of the drip tray 212. The lower tongue 305 slides beneath the bottom surface 311 of the housing 215, while the upper tongue 307 enters into the opening 313 in the housing 215 and snap-fittingly engages with the housing 215. The upper tongue 307 includes a flexible web portion 308, a lower cross bar 315 and an upper cross bar 317 located above the lower cross bar 315 at the end of the tongue 307.

The snap-fit engagement mechanism is further illustrated in FIGS. 48 and 49. As can be seen, the housing 215 includes a ramp 318, which terminates in a vertical retaining ridge 319. In operation, the upper tongue 307 flexes up and the lower cross bar 315 snaps over the retaining ridge 319, thus preventing removal of the drip tray 212 by simply pulling it out. In order to remove the drip tray 212, a screwdriver (or similar) tool (FIG. 49) is used to reach in from the front through the opening 313 to engage the upper cross bar 317 and then flex the tongue 307 upwards to allow removal of the drip tray 212. The housing 215 also has a flexure 321, which preloads the lower tongue 305 into a channel 323 on the housing 215.

In one embodiment, the drip tray 212 is further pre-loaded into place. In this connection, the drip tray 212 includes a spherical area which matches the bottom spherical shape of the canister 227. The drip tray 212 raised bumps, e.g., 325, FIG. 48, that protrude and create a small physical interference between the drip tray 212 and canister 227. In operation, the act of installing/snapping the canister 227 into the housing 215 applies force to the drip tray 212, preloading it into place. Thus, the spherical interface acts as a locking mechanism in addition to the snap-fit feature implemented by the cross bar 315 engaging the retaining ridge 319. So, if the snap-fit engagement were to fail for some reason, the drip tray 212 remains non-removable as long as the canister 227 is in place.

FIGS. 50-53 illustrate a tabletop configuration 311 for attaching liquid dispensers according to illustrative embodiments to a flat horizontal surface. The configuration includes a horizontal base portion 321 with an arced depression 323 shaped to receive the bottom of the housing 215 and a ribbed rectangular vertical structure 325 configured to attach to the housing 215 in a manner similar to that of a back plate such as back plate 213 or 13. In one embodiment, the arced depression 323 has a channel 324 therein into which the lower tongue of the drip tray 212 fits. A cover component 331 may be provided to cover the channel 324 in embodiments which do not employ a drip tray 212.

In one embodiment, an intermediate plate 329 is screwed to the base 321 via fasteners, e.g. 322, and provides a bearing surface for fasteners which secure the complete assembly to a mounting surface. There are four thru holes 326 in the base 321 that align to counterbored holes 328 in the plate 329. For tooling reasons, in an illustrative embodiment, the bearing surface for the fasteners cannot be included in the base 321, so an intermediary part is required to create the bearing surface. The plate 329 additionally creates retention points for the cover component 331 and, in particular, slotted retention holes 330 with which the flexures 332 in the cover component 331 interface.

A second plate 327 serves as a closure for the underside of the assembly and has four through holes 334 which align with the mounting holes 326, 328 in the base 321 and the plate 329. In one embodiment, the plate 327 is fabricated of metal such as stainless steel and directly bears against an underside mounting surface. If adhesion is used, this plate 327 would be adhered to the mounting surface.

An alternative embodiment is one where base 327 utilizes threaded inserts to accept fasteners passing through the counterbores 326 in base 321, bearing against surface plate 329. In this embodiment, the bottom plate 327 is adhered to an external mounting surface. Removal of the just mentioned fasteners permits the plate 327 to separate from the rest of the assembly, leaving the plate 327 adhered to the external mounting surface. In lieu of adhesive, plate 327 may have through holes, allowing 327 to be fastened to the mounting surface.

Figure 55:
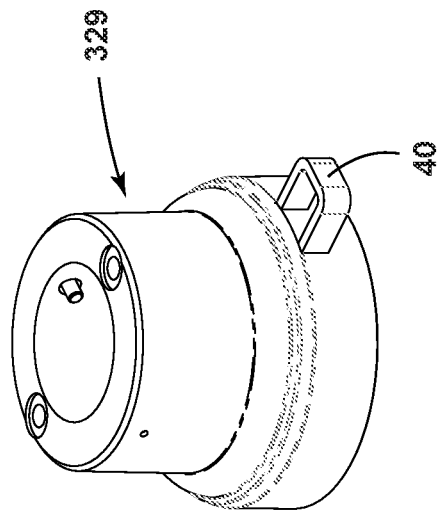
FIG. 55 is a perspective view illustrating the closure and closure shroud in an assembled state.
Figure 56:
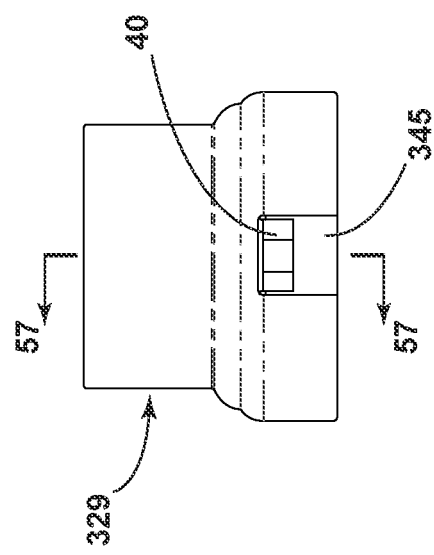
FIG. 56 is a side view of the assembled closure and closure shroud.
Figure 54:
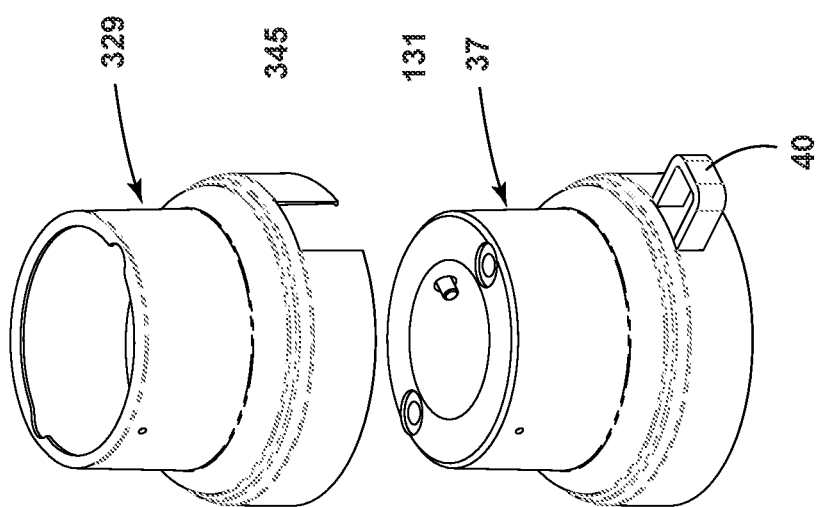
FIG. 54 is an exploded perspective view illustrating a closure and a closure shroud according to an illustrative embodiment.
Figure 58:
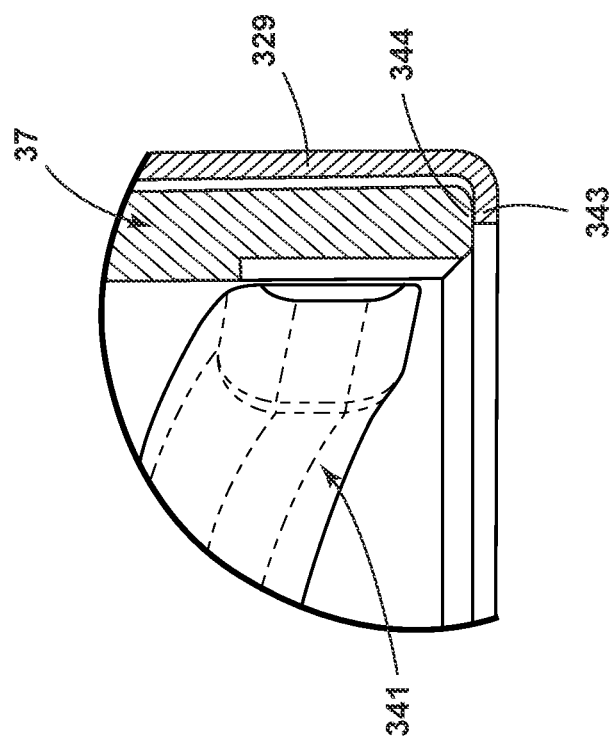
FIG. 58 is a view of a detail of a portion of FIG. 57.

FIGS. 54 and 55 illustrate an embodiment where a cover (shroud) 329 is employed to encase the exterior of the plastic closure 37 of FIG. 7. In one embodiment, the shroud 329 may be a stamped stainless steel cover, which forms a new bearing surface on which the inner cylindrical metal pump top 35 rides. In such an embodiment, the inner cylindrical metal pump top 35 may be coated with a material with a low coefficient of friction like PTFE (Teflon) that is highly resistant to abrasion.

Figure 57:
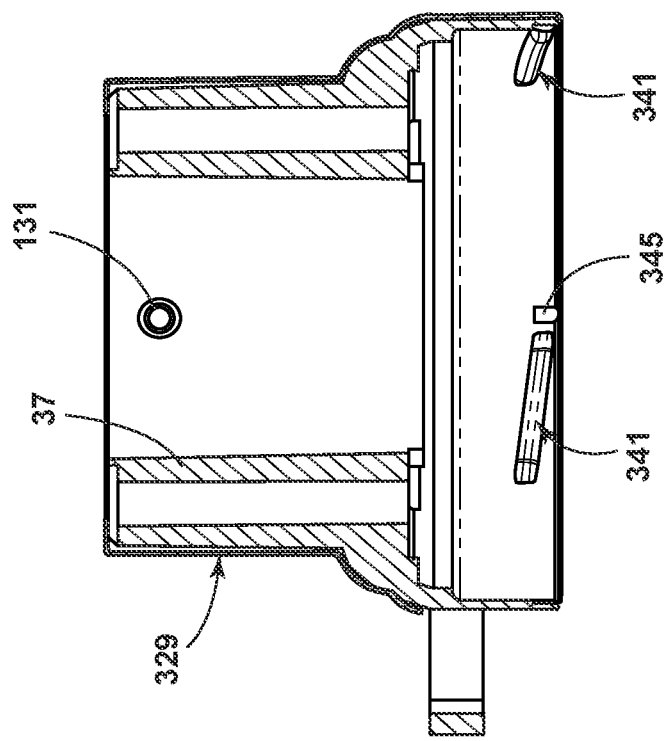
FIG. 57 is a sectional view taken at 57-57 of FIG. 56.
Figure 59:
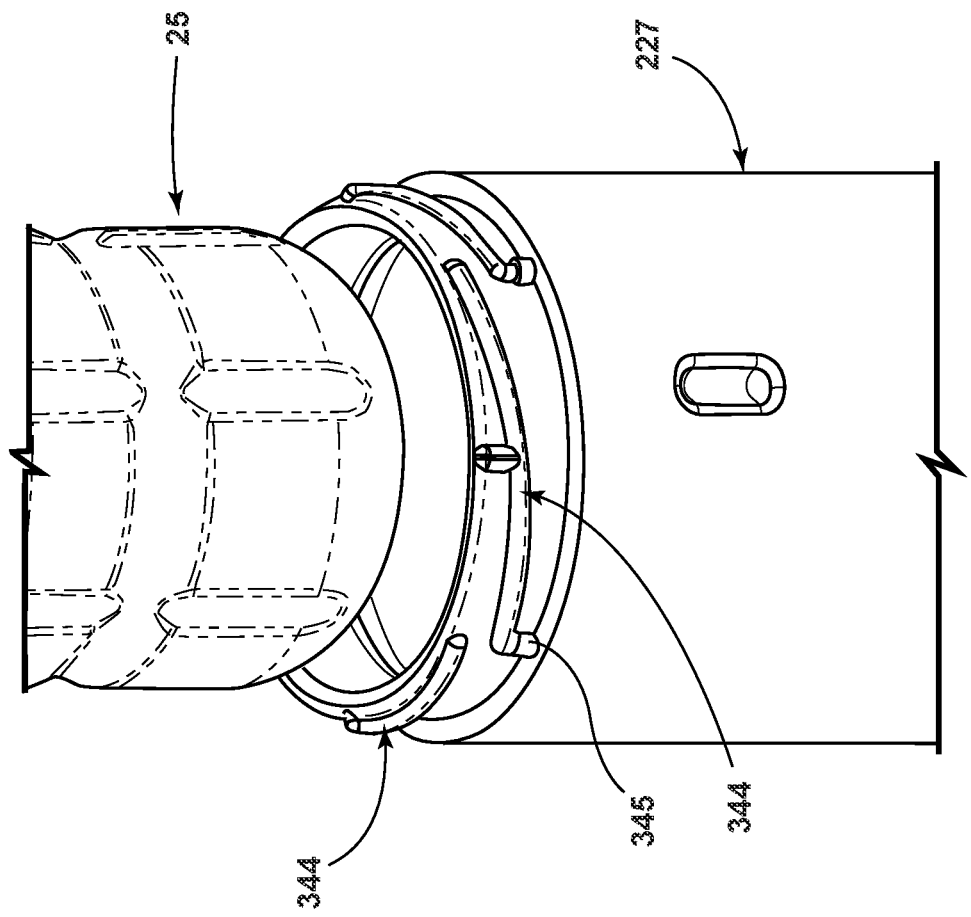
FIG. 59 is a partial perspective view illustrating one embodiment of threads on a canister for engaging threads on a mating closure.

Feature 345 in FIGS. 57 and 59 is a detent in the plastic closure 37 which sets a final position for the threaded engagement provided by threads, e.g. 341, which engage cooperating threads, e.g. 345, on the canister 227. Thus, as the closure 37 is threaded onto the canister 227, a feature in the thread will set itself at that detent. The shroud 329 may also be secondarily affixed to the closure 37 with an adhesive.

It should also be noted that the dispenser can still properly operate without the stainless steel shroud 329. However, the shroud 329 provides a more robust bearing surface with closer tolerance, in addition to allowing for a draft angle on the closure to facilitate extraction during a molding process for forming the closure. In one embodiment, the shroud 329 is thin walled, having a thickness, for example, in one embodiment is 0.0125 inches but may vary in other embodiments.

Figure 60:
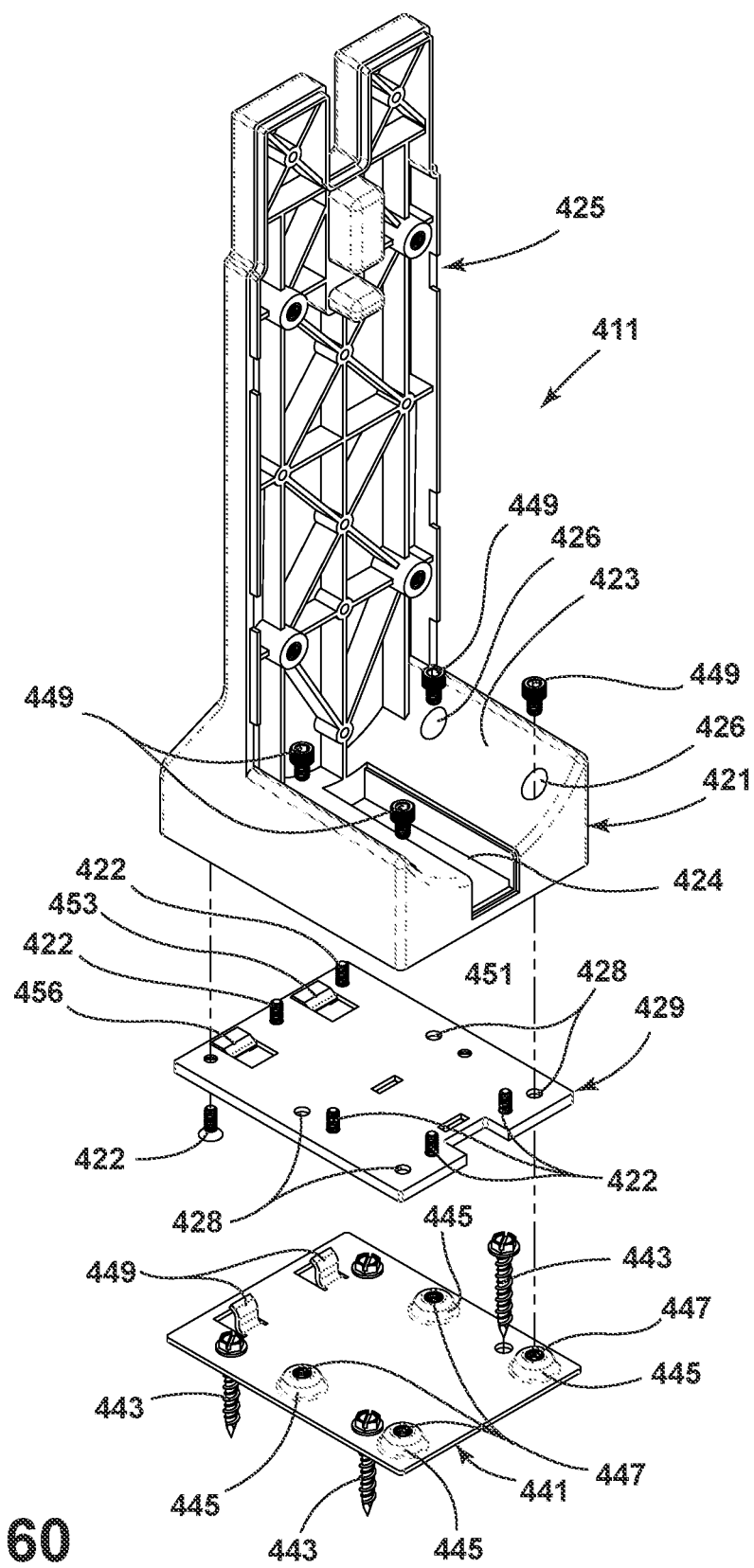
FIG. 60 is an exploded perspective of another tabletop mount embodiment.
Figure 61:
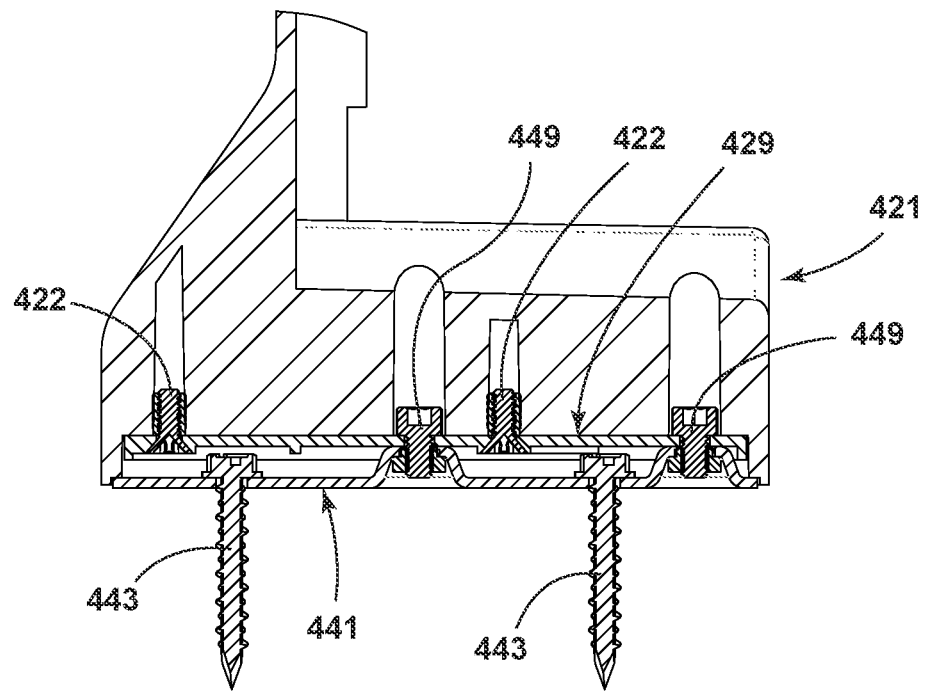
FIG. 61 is a sectional view of the assembled embodiment of FIG. 60 taken on a plane bisecting the screws which attach the assembly to a tabletop.
Figure 62:
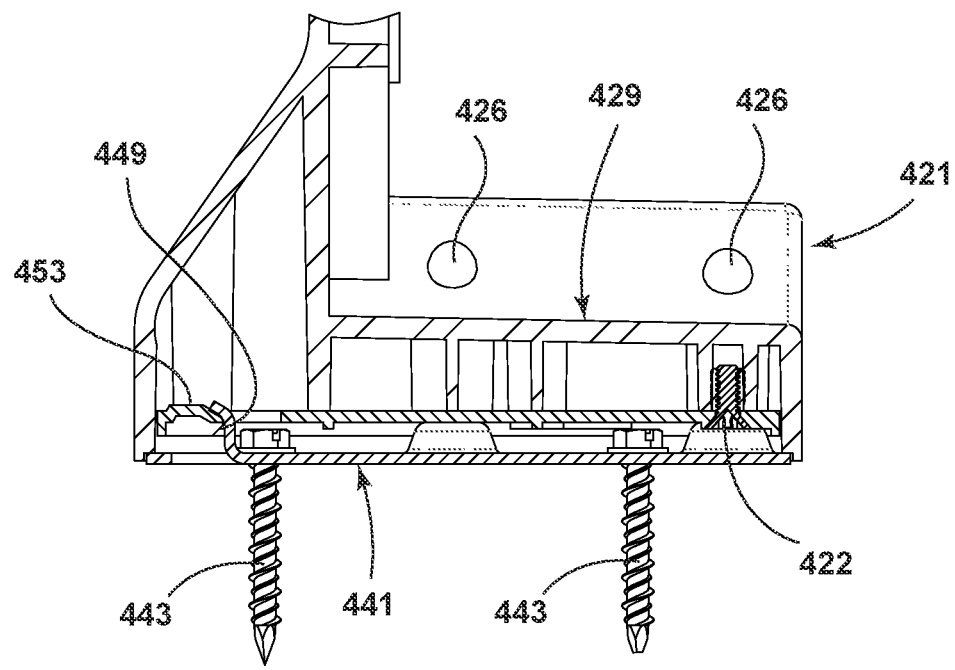
FIG. 62 is a sectional view of the assembled embodiment of FIG. 60 taken on a plane bisecting a hook feature of a base plate component of the embodiment.

FIGS. 60-62 illustrate another embodiment of a tabletop mounting platform 411 for attaching liquid dispensers according to illustrative embodiments to a flat horizontal surface. The platform 411 again includes a horizontal base portion 421 with an arced depression 423 shaped to receive the bottom of the housing 215 and a ribbed rectangular vertical structure 425 configured to attach to the housing 215 in a manner similar to that of a back plate such as back plate 213 or 13. In one embodiment, the arced depression 423 again has a channel 424 therein into which the lower tongue of the drip tray 212 fits.

In the embodiment of FIGS. 60-62, an intermediate plate 429 is screwed to the base 421 via fasteners, e.g. 422. There are four through holes, e.g. 426 in the base 421 that align with holes 428 in the intermediate plate 429.

A metal base plate 441 may be attached to a mounting surface by screws, e.g. 443, or by bonding tape, or a liquid bonding agent, and includes four raised bosses 445 with threaded holes 447 therein. A pair of retention hooks 449 at the rear of the metal base plate 441 further engage openings 451 at the rear of the intermediate plate 429 to further secure the intermediate plate 429 in position. As seen in FIG. 62, a slight interference fit is created between the hooks 449 and surfaces 453 of the intermediate plate 429, which allows the metal base plate to "pull" the assembly downward creating a pre-load at the rear.

To attach the assembly together, the intermediate plate 429 with base 421 attached is hooked onto the hooks 449 of the metal base plate 441 and rotated into position. Fasteners 449 are then passed through the holes 426 in the base 421, through the holes 428 in the intermediate plate 429, and screwed into the threaded bosses 445. The embodiment of FIGS. 60-62 has the advantage that the base/intermediate plate assembly may be removed together without detaching the metal base plate 441 from the tabletop.

A cover component may again be provided to cover the channel 424 in embodiments which do not employ a drip tray 212. In one embodiment, a cover component 331 is pressed in by pushing downward in a vertical direction. There are two vertical legs or "fingers" protruding from the cover's underside with a barb at their tips. The legs will flex over two vertical slides as the cover component is pushed downward. The barbs will then snap into retaining features in the vertical slides that hold the cover component in place. To remove the cover component, a screw driver or similar tool is inserted into a release cavity to promote outward flex of the front leg and barb, thus, releasing the front of the cover component for upward rotation, thus freeing the back leg and promoting vertical removal.

From the foregoing, those skilled in the art will appreciate that various adaptations and modifications of the just described illustrative embodiments can be configured without departing from the scope and spirit of the invention. For example, a foaming pump may be substituted for the disclosed pump to pump liquids in foamed form such as, for example, and without limitation, hair products, skin products and hygienic products such as hair shampoo, body wash, hand soap, hand sanitizer, and antibacterial skin soap. In various illustrative embodiments, for corrosion resistance, the metallic parts may either be stainless steel, anodized, lacquered, and/or powder coated. Therefore, it is to be understood that, within the scope of the appended claims, the invention may be practiced other than as specifically described herein.

What is claimed is:

1. A liquid dispenser apparatus comprising:
   (a) a back plate, a housing, and a liquid dispenser unit, the housing and backplate being constructed to attach to one another, the housing and liquid dispenser unit being constructed such that the liquid dispenser unit is removably installable into the housing and pivotally mounted with respect thereto such that the dispenser unit is pivotable to a selected acute angle with respect to the housing;
(b) the liquid dispenser unit comprising a pump, a pump top, a closure removably attached to the pump and having a lower skirt portion, a reservoir for storing liquid to be dispensed, and a canister, the canister being shaped to receive and house the reservoir;
(c) the reservoir comprising a plastic material, the pump and reservoir being attached to one another with a leak-proof seal formed between the reservoir and the pump;
(d) the lower skirt portion including a hook on a side surface thereof, the lower skirt portion and canister being configured to removably attach together;
(e) the pump top comprising four mating components including a top cap component, a bottom cap component, and upper and lower intermediate components, the top cap component including two threaded bosses on an underside thereof, the upper and lower mating intermediate components having mating openings and mating notches formed therein, the lower intermediate component further having a liquid dispensing opening, a liquid receiving boss, and first and second vertically depending tangs formed on either side of the liquid dispensing opening, the tangs being configured to snap-fittingly engage a liquid dispensing opening of the bottom cap component;
(f) an interior rear surface of the housing including first and second back surface positioning arms, first and second resilient side retaining arms, and first and second side pivot bumps;
(g) the first and second side pivot bumps being positioned to fit into respective pivot notches formed on opposite lower sides of the canister to enable pivotal movement of the canister with respect to the housing about a horizontal axis defined by the first and second side pivot bumps;
(h) the ends of the first and second resilient side retaining arms being configured to snap into respective indentations in an outer surface of the canister in order to position and retain the liquid dispenser unit in an installed position in the housing;
(i) the first and second back surface positioning arms being positioned to support a back surface of the canister; and
(j) a locking mechanism comprising a ferromagnetic locking pin insertable into an aperture in the rear of the housing and through the opening in the hook of the lower skirt portion.

2. The liquid dispenser apparatus of claim 1 wherein the upper and lower intermediate components of the pump top are fused together to create a hollow, sealed assembly which provides a path through which a stored liquid travels to the dispensing opening in the lower intermediate component and then to the dispensing opening in the bottom cap component;
wherein a stem of the pump passes through the hole in the bottom cap component and fits into the boss of the lower intermediate component to enable supply of the stored liquid to the fused together intermediate components;
wherein the top and bottom cap components sandwich the fused-together intermediate components; and
wherein, in assembly, first and second guide pins pass through the holes in the bottom cap component, through the holes and notches in each of the intermediate components, and thread into the threaded bosses on the underside of the top cap component.

3. The liquid dispenser apparatus of claim 1 wherein the lower skirt portion and canister threadably engage with one another.

4. The liquid dispenser apparatus of claim 1 wherein the pump has a track formed on a side surface thereof shaped to engage a pin on the closure and configured to enable the pump to removably attach to the closure.

5. The liquid dispenser apparatus of claim 1 wherein the reservoir comprises one of (a) a cylindrical cartridge or (b) a plastic bag.

6. The liquid dispenser apparatus of claim 1 wherein a hook is positioned on the back of the canister and configured to engage first and second latches formed on the housing in order to facilitate removable attachment of the canister to the housing.

7. The liquid dispenser apparatus of claim 1 further comprising a bottom tang positioned on the back of the canister and mountable in a groove formed in the housing in order to facilitate removable attachment of the canister to the housing.

8. The liquid dispenser apparatus of claim 1 further comprising a drip tray positioned beneath the housing and removably attachable thereto.

9. The liquid dispenser apparatus of claim 8 wherein the drip tray comprises first and second horizontally projecting tongues which comprise part of a snap-fit attachment mechanism for attaching the drip tray to the housing.

10. A liquid dispenser apparatus comprising:
(a) a back plate, a housing, and a liquid dispenser unit, the housing and backplate being constructed to attach to one another, the housing and liquid dispenser unit being constructed such that the liquid dispenser unit is removably installable into the housing and pivotally mounted with respect thereto such that the dispenser unit is pivotable to a selected acute angle with respect to the housing;
(b) the liquid dispenser unit comprising a pump, a pump top, a closure removably attached to the pump and having a lower skirt portion, a reservoir for storing liquid to be dispensed, and a canister, the canister being shaped to receive and house the reservoir;
(c) the reservoir comprising a plastic material, the pump and reservoir being connected together, with a leak-proof seal established between the pump and reservoir;
(d) the lower skirt portion including a hook on a side surface thereof, the lower skirt portion and canister being configured to removably attach together;
(e) an interior rear surface of the housing including first and second back surface positioning arms, first and second resilient side retaining arms, and first and second side pivot bumps;
(f) the first and second side pivot bumps being positioned to fit into respective pivot notches formed on opposite lower sides of the canister to enable pivotal movement of the canister with respect to the housing about a horizontal axis defined by the first and second side pivot bumps;
(g) the ends of the first and second resilient side retaining arms being configured to snap into respective indentations in an outer surface of the canister in order to position and retain the liquid dispenser unit in an installed position in the housing;

(h) the first and second back surface positioning arms being positioned to support a back surface of the canister; and (i) a locking mechanism comprising a ferromagnetic locking pin insertable into an aperture in the rear of the housing and through the opening in the hook of the lower skirt portion.

11. The liquid dispenser apparatus of claim 10 wherein the lower skirt portion and canister threadably engage with one another.

12. The liquid dispenser apparatus of claim 10 wherein the pump has a track formed on a side surface thereof shaped to engage a pin on the closure and configured to enable the pump to removably attach to the closure.

13. The liquid dispenser apparatus of claim 10 wherein the reservoir comprises one of (a) a cylindrical cartridge or (b) a plastic bag.

14. The liquid dispenser apparatus of claim 10 wherein the canister has an attachment member positioned on a back surface thereof and shaped to engage first and second latches formed on the housing so as to enable removable attachment of the canister to the housing.

15. The liquid dispenser apparatus of claim 10 further comprising a bottom tang positioned on a back of the canister and mountable in a groove formed in the housing in order to facilitate removable attachment of the canister to the housing.

16. The liquid dispenser apparatus of claim 10 further comprising a drip tray positioned beneath the housing and removably attachable thereto.

17. The liquid dispenser apparatus of claim 16 wherein the drip tray comprises first and second horizontally projecting tongues which comprise part of a snap-fit attachment mechanism for attaching the drip tray to the housing.

18. A liquid dispenser apparatus comprising:

(a) a back plate, a housing, and a liquid dispenser unit, the housing and backplate being constructed to attach to one another, the housing and liquid dispenser unit being constructed such that the liquid dispenser unit is removably installable into the housing and pivotally mounted with respect thereto such that the dispenser unit can be pivoted to a selected acute angle with respect to the housing;

(b) the liquid dispenser unit comprising a pump, a pump top, a closure removably attached to the pump and having a lower skirt portion, and a canister for storing liquid to be dispensed;

(c) the lower skirt portion including a u-shaped hook on a side surface thereof, the lower skirt portion and canister being configured to removably attach together;

(d) the pump top comprising four mating components including a top cap component, a bottom cap component, and upper and lower intermediate components, the top cap component including two threaded bosses on an underside thereof, the upper and lower mating intermediate components having mating openings and mating notches formed therein, the lower intermediate component further having a liquid dispensing opening, a liquid receiving boss, and first and second vertically depending tangs formed on either side of the liquid dispensing opening, the tangs being configured to snap-fittingly engage a liquid dispensing opening of the bottom cap component;

(e) an interior rear surface of the housing including first and second back surface positioning arms, first and second resilient side retaining arms, and first and second side pivot bumps;

(f) the first and second side pivot bumps being positioned to fit into respective pivot notches formed on opposite lower sides of the canister to enable pivotal movement of the canister with respect to the housing about a horizontal axis defined by the first and second side pivot bumps;

(g) the ends of the first and second resilient side retaining arms being configured to snap into respective indentations in an outer surface of the canister in order to position and retain the liquid dispenser unit in an installed position in the housing;

(h) the first and second back surface positioning arms being positioned to support the back surface of the canister; and (i) a locking mechanism comprising a ferromagnetic locking pin insertable into an aperture in the rear of the housing and through the opening in the hook of the lower skirt portion.

19. The liquid dispenser apparatus of claim 14 so configured that, to remove the canister, the canister is rotated forward to said acute angle wherein it rests under its own weight and wherein physically pulling the canister further downward causes a shoulder surface of the attachment member to react with a surface of the housing so as to disengage the canister from the side pivot bumps.

20. The liquid dispenser apparatus of claim 17 wherein the snap-fit engagement mechanism further comprises a ramp having a vertical retaining ridge and wherein a first horizontally projecting upper tongue flexes up and a lower cross bar of the upper tongue snaps over the retaining ridge thus preventing removal of the drip tray by simply pulling it out.

21. The liquid dispenser apparatus of claim 20 further configured such that a tool is insertable through an opening in the housing so as to engage an upper cross bar of the upper tongue and then flex the upper tongue upwards to allow removal of the drip tray.

22. The liquid dispenser apparatus of claim 21 wherein the housing further includes a flexure which preloads a lower horizontally projecting tongue into a channel of the housing.

23. The liquid dispenser apparatus of claim 16 wherein the drip tray includes a spherical area which matches a bottom spherical shape of the canister and further includes one or more raised bumps which protrude and create a physical interference between the drip tray and canister such that the act of installing the canister into the housing applies force to the drip tray, preloading it into place.

24. The liquid dispenser apparatus of claim 10 further comprising a shroud shaped to encase the exterior of the closure and which provides a bearing surface on which the pump top rides.

25. The liquid dispenser apparatus of claim 1 wherein the housing includes an upper portion having parallel outer side surfaces and a circularly contoured inner surface which is shaped and dimensioned to partially surround, protect and shield the pump top.

26. The liquid dispenser apparatus of claim 10 wherein the housing includes an upper portion having parallel outer side surfaces and a circularly contoured inner surface which is shaped and dimensioned to partially surround, protect and shield the pump top.

27. The liquid dispenser apparatus of claim 1 further comprising a shroud shaped to enclose the exterior of the closure and which provides a bearing surface on which the pump top rides.

28. The liquid dispenser apparatus of claim 18 further comprising a shroud shaped to enclose the exterior of the closure and which provides a bearing surface on which the pump top rides.

* * * * *